(12) United States Patent
Chapman et al.

(10) Patent No.: US 8,560,097 B1
(45) Date of Patent: *Oct. 15, 2013

(54) COMPUTER ASSISTED METHOD FOR REMOTELY MONITORING A SITE FOR ANTICIPATED FAILURE AND MAINTENANCE WITH A PLURALITY OF CONTROLS

(75) Inventors: Frank Marion Chapman, Houston, TX (US); Ronald Lyle Brown, Houston, TX (US)

(73) Assignee: Ashford Technical Software, Inc., Houston, TX (US)

( * ) Notice: Subject to any disclaimer, the term of this patent is extended or adjusted under 35 U.S.C. 154(b) by 845 days.

This patent is subject to a terminal disclaimer.

(21) Appl. No.: 12/766,604

(22) Filed: Apr. 23, 2010

Related U.S. Application Data

(60) Provisional application No. 61/214,750, filed on Apr. 28, 2009.

(51) Int. Cl.
| | |
|---|---|
| E21B 43/12 | (2006.01) |
| E21B 47/00 | (2012.01) |
| G01F 1/00 | (2006.01) |
| G01F 1/50 | (2006.01) |
| G01F 23/00 | (2006.01) |
| G01N 11/00 | (2006.01) |
| G01V 3/18 | (2006.01) |
| G05B 11/01 | (2006.01) |
| G05B 13/02 | (2006.01) |
| G05B 15/00 | (2006.01) |
| G05B 15/02 | (2006.01) |
| G05B 21/02 | (2006.01) |
| G05D 7/00 | (2006.01) |
| G05D 9/00 | (2006.01) |
| G06F 3/00 | (2006.01) |
| G06F 17/00 | (2006.01) |
| G06F 17/21 | (2006.01) |
| G06F 17/22 | (2006.01) |
| G06F 17/24 | (2006.01) |
| G06F 17/30 | (2006.01) |
| G06F 19/00 | (2011.01) |

(52) U.S. Cl.
USPC ........ 700/83; 700/9; 700/12; 700/51; 700/73; 700/108; 700/117; 700/281; 700/282; 166/53; 166/250.01; 702/9; 702/12; 702/45; 702/47; 702/50; 702/100; 702/182; 707/790; 715/205; 715/215; 715/224; 715/227; 715/733

(58) Field of Classification Search
USPC ............. 700/9, 12, 51, 73, 83, 108, 117, 281, 700/282; 166/53, 250.01; 702/9, 12, 45, 47, 702/50, 100, 182; 707/709; 715/205, 215, 715/224, 227, 733
See application file for complete search history.

(56) References Cited

U.S. PATENT DOCUMENTS

| | | | | |
|---|---|---|---|---|
| 5,465,798 | A * | 11/1995 | Edlund et al. | 175/24 |
| 6,176,323 | B1 * | 1/2001 | Weirich et al. | 175/40 |

(Continued)

Primary Examiner — Mohammad Ali
Assistant Examiner — Jennifer L Norton
(74) Attorney, Agent, or Firm — Buskop Law Group, PC; Wendy Buskop

(57) ABSTRACT

A computer assisted method to monitor a status from a secondary location of a plurality of equipment on a drilling site, while simultaneously enabling preventive maintenance is described herein. A user can view at least one cycle, at least one control state, and at least one pressure. The user can also view equipment information, equipment repair history, and other information necessary to ensure that a piece of equipment has minimal down time.

5 Claims, 17 Drawing Sheets

(56) References Cited

U.S. PATENT DOCUMENTS

| | | |
|---|---|---|
| 6,378,628 B1 * | 4/2002 | McGuire et al. ............... 175/48 |
| 2004/0230328 A1 * | 11/2004 | Armstrong et al. ............ 700/83 |
| 2005/0033466 A1 * | 2/2005 | Eryurek et al. ............... 700/108 |
| 2005/0240289 A1 * | 10/2005 | Hoyte et al. ..................... 700/49 |
| 2007/0067725 A1 * | 3/2007 | Cahill et al. .................. 715/733 |
| 2009/0044977 A1 * | 2/2009 | Johnson et al. ................. 175/24 |
| 2012/0041574 A1 * | 2/2012 | Hsiung et al. .................. 700/47 |
| 2013/0138254 A1 * | 5/2013 | Seals et al. ..................... 700/282 |

\* cited by examiner

US 8,560,097 B1

COMPUTER ASSISTED METHOD FOR REMOTELY MONITORING A SITE FOR ANTICIPATED FAILURE AND MAINTENANCE WITH A PLURALITY OF CONTROLS

CROSS REFERENCE TO RELATED APPLICATIONS

The present application claims priority and benefit of U.S. Provisional Patent Application Ser. No. 61/214,750 filed on Apr. 28, 2009, entitled "SYSTEM AND METHOD FOR COLLECTING, ARCHIVING AND VIEWING DATA FROM INDUSTRIAL OPERATING FACILITIES VIA THE INTERNET". This reference is hereby incorporated in its entirety.

FIELD

The present embodiments generally relate to a computer assisted method for monitoring a status from a secondary location of a plurality of equipment on a drilling site, while simultaneously enabling preventive maintenance of the plurality of equipment.

BACKGROUND

A need exists for a simple method operable without the need for training to detect changes in state of various components or parts of components used to drill oil and natural gas wells, or water wells that can be viewed locally, within a few feet of a site, or remotely, thousands of miles away, simultaneously, and allow for maintenance planning.

A need exists for a computer assisted method that continuously and automatically monitors onshore and offshore drilling operations to ensure safe, efficient, and cost effective drilling operations.

A need exists for a computer assisted method that can track equipment utilization, equipment cycles, and valve cycles to provide for preventative maintenance, elimination of costly downtime, environmental protection, and an increase in safety by identifying equipment in need of repair and maintenance.

A need exists for a computer assisted method that can track information associated with a drilling operation including a historical status of the drilling and safety equipment, particularly when the drilling operation is at a remote location that can take several days to reach.

A further need exists for a computer assisted method that allows management, drilling experts, and other operations personnel to remain physically remote from the drilling site while having easy and timely access to the status of a drilling operation and safety equipment.

The present embodiments meet these needs.

BRIEF DESCRIPTION OF THE FIGURES

The detailed description will be better understood in conjunction with the accompanying drawings as follows.

Figure 1:
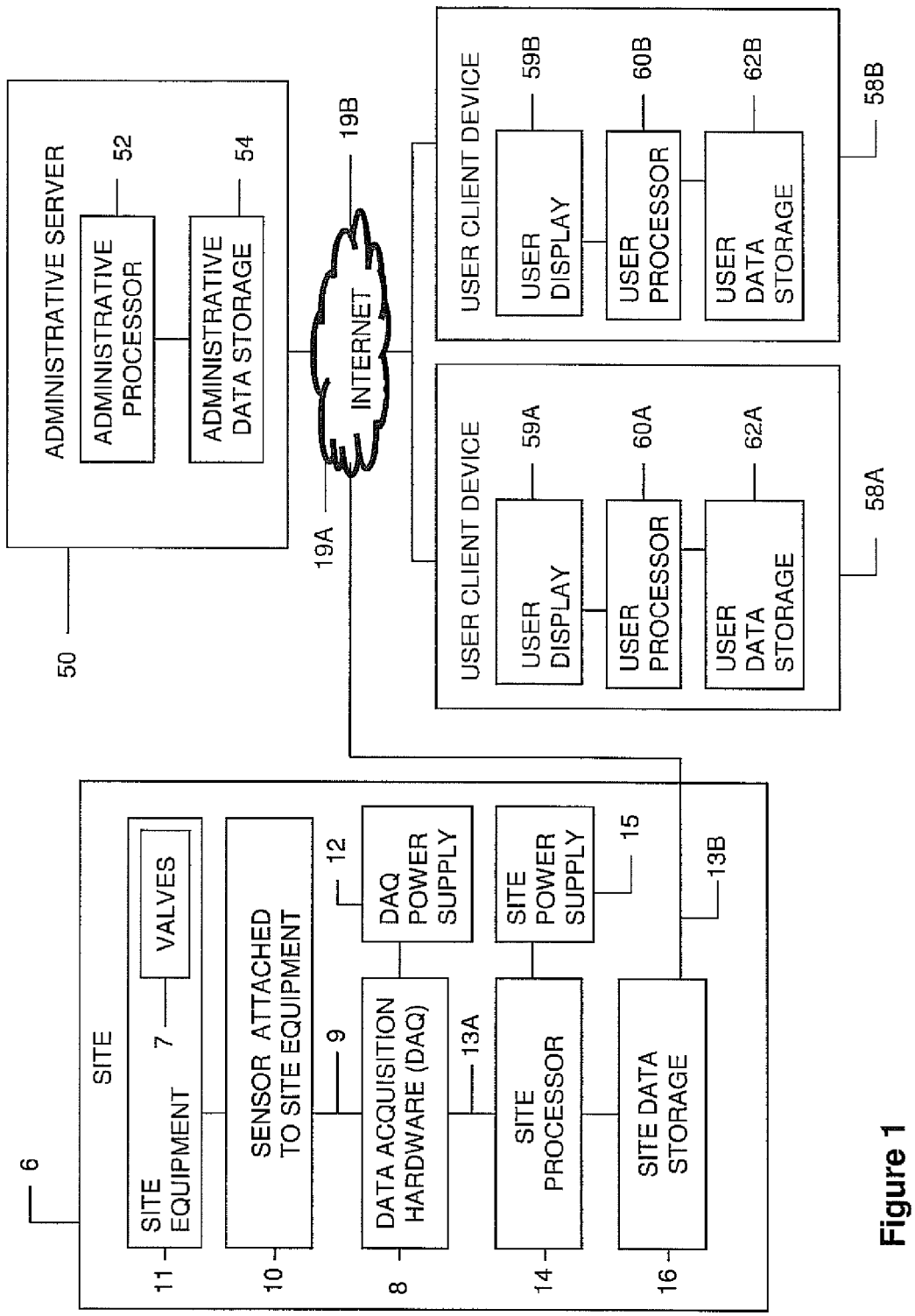
FIG. 1 is a diagram of the computer assisted method.

The present embodiments are detailed below with reference to the listed Figures.

DETAILED DESCRIPTION OF THE EMBODIMENTS

Before explaining the present computer assisted method in detail, it is to be understood that the computer assisted method is not limited to the particular embodiments and that it can be practiced or carried out in various ways.

The present embodiments relate to a system, a method, and a computer assisted method for monitoring a status from a secondary location of a plurality of equipment on a site, such as a drilling rig for drilling natural gas or oil wells, while simultaneously enabling preventive maintenance for the plurality of equipment on the site.

The system, the method, or the computer assisted method can be used to continuously and automatically monitor onshore and offshore drilling operations to ensure safe, efficient, and cost effective drilling operations. Repairing drilling and safety equipment during a drilling operation can be time consuming and costly. For example, in an offshore drilling operation, replacing a $25.00 valve on a subsea blowout preventer can cause two or three days of lost drilling time and several thousand dollars in added costs.

The system can be used for tracking equipment utilization, equipment cycles, and valve cycles to provide for preventative maintenance, elimination of costly downtime, environmental protection, and an increase in safety by identifying equipment in need of repair and maintenance. For example, equipment failure during a drilling operation can lead to blowouts that endanger personnel, endanger equipment, and can have a sever impact on the environment.

The system, the method, and the computer assisted method can save fossil fuels by improving operational efficiency and eliminating unnecessary activities.

The system, the method, and the computer assisted method can protect the environment by eliminating the accidental release of toxic material that can result from equipment failure or operational failure.

A drilling operator can trouble-shoot a problem at the drilling site, even if the experienced personnel of the drilling operator are not physically at the drilling site.

A system, the method, and the computer assisted method to monitor a status from a secondary location of a plurality of equipment on a drilling site, while simultaneously enabling preventive maintenance is described herein.

In an embodiment, the site equipment can be a valve, a blow out preventer, other drilling equipment, a pressure line in a subsea umbilical, or combinations thereof.

In an embodiment, the sensor data can be a digital signal, an analog signal, a message, a report, or combinations thereof. Examples of the message, the report, a presentation, or a document and user administration item for selection by a user can include at least one control status chart, at least one control status table, at least one pressure chart, at least one pressure table, at least one control cycle, at least one valve cycle, at least one selected rig, and a log out. Other reports and presentations can include a pressure change details report At a site, the system, the method, and the computer assisted method can have data acquisition hardware for receiving and storing sensor data from a sensor attached to a piece of equipment at the site.

The system, the method, and the computer assisted method can have a site processor in communication with a site data storage for receiving the sensor data from the data acquisition hardware. The site processor can be a computer or a server. The sensor data can be transmitted to an administrative server via a network. The network can include the Internet.

In an embodiment, the site process monitor can have computer instructions in the site data storage to monitor a status of a digital input monitor, an analog input monitor, a data transfer device, an analog detail monitor, a site task processor device, or combinations thereof.

The system, the method, and the computer assisted method can have computer instructions in the site data storage for forming a database for the sensor data.

The system, the method, and the computer assisted method can have a digital input monitor in the site data storage, an analog input monitor in the site data storage, an analog detail monitor in the site data storage, a data transfer device in the site data storage, a site task device in the site data storage, or combinations thereof.

In an embodiment, the digital input monitor can have computer instructions in the site data storage for monitoring digital sensor data from the data acquisition equipment, computer instructions in the site data storage to compare digital sensor data to determine if a change in the digital sensor data occurs and to store the data once a change occurs, or computer instructions in the site data storage to store digital sensor data after a preset number of cycles.

The digital input monitor can read the sensor data on a periodic cycle and can mask any unused digital bits. The digital input monitor can determine if a change in the digital sensor information and sensor data occurs. For example, if the digital data changes, these computer instructions can store both the original digital data and the changed digital data to the database, as well as a timestamp of the changes.

The digital input monitor can store sensor data to the site database after a preset number of cycles, even if the digital data is unchanged. For example, for a blowout preventer ram on an oil rig, the digital input monitor can determine whether the ram cycled and store this information to the site database. The digital input monitor can also timestamp this information to indicate when the ram cycle occurred.

In an embodiment, the analog input monitor can have computer instructions in the site data storage for monitoring analog sensor data from the data acquisition equipment, computer instructions in the site data storage to compare analog sensor data to determine if a change in the analog sensor data occurs and to store the data once a change occurs, or computer instructions in the site data storage to store analog sensor data after a preset number of cycles.

The analog input monitor can monitor voltage and current data from the data acquisition hardware on a periodic time cycle. The analog input monitor can determine if a change in sensor voltage or current is significant. If the change is significant, both the previous voltage and the current voltage or current data can be stored to the database along with a timestamp indicating when the change occurred.

The analog input monitor can store sensor data in the site data storage after a preset number of cycles even if the sensor data is unchanged, such as storing sensor data after every 25 cycles.

In an embodiment, the data transfer device can have computer instructions in the site data storage to transmit the sensor data sensor data stored by the digital input monitor, the analog input monitor, the analog detail monitor, or combinations thereof.

In an embodiment, the data transfer device can have computer instructions in the site data storage to verify a transfer of the digital sensor data and the analog sensor data is complete, or computer instructions in the site data storage to mark the digital sensor data and the analog sensor data as transferred.

In an embodiment, the data transfer device can have computer instructions to transmit at least one message and at least one report stored by the digital input monitor, the analog input monitor, the analog detail monitor, the data transfer device, the site process monitor and the site task device.

The data transfer device can verify that a transfer of sensor data is complete. The data transfer device can verify the occurrence of a transfer by receiving either a positive response or a negative response from the administrative server.

The data transfer device can mark sensor data as transferred once the transfer occurs. If a positive response is received, the data in the database can be marked as transferred. If a negative response is received, the data is not marked as transferred and additional transfer attempts can be made at a later time. Marking of the information and data can occur by setting a data transfer indicator associated with the particular data item in the database.

In an embodiment, the site task device can have computer instructions in the site data storage to generate a report on disk utilization, computer instructions in the site data storage to execute an operating system utility command, or computer instructions in the site data storage to perform another computer system maintenance activity. Another computer system maintenance activity can create a list of the programs running on the computer. The list can include the memory and central processor utilization for each program running on the computer.

The system, the method, and the computer assisted method can have a site process monitor in the site data storage for monitoring the digital input monitor, the analog input monitor, the analog detail monitor, the data transfer device, and the site task device.

The site process monitor can start or end all of the other monitors and devices.

In an embodiment, the site process monitor can have computer instructions in the site data storage to monitor a status of the digital input monitor, the analog input monitor, the data transfer device, the analog detail input monitor, the site task device, or combinations thereof. This multiple device monitoring occurs by periodically polling each monitor or device to determine if it is currently running and if it is functioning correctly.

The system, the method, and the computer assisted method can have an analog detail monitor in the site data storage. The analog detail monitor can have computer instructions in the site data storage for monitoring analog data from the data acquisition equipment. The analog detail monitor can have computer instructions in the site data storage to compare analog sensor data to detect a change in analog sensor data.

The analog detail monitor can monitor sensor data on a rapid data sampling cycle and continuously save the sensor data to a data buffer. When the analog detail monitor detects a significant change in either voltage or current, additional data can be added to the buffer until a full window of data has been collected. When a complete window of data has been collected, it can be saved to the database.

The term "rapid sampling rate" as used herein means changes in voltage or current data that can occur within 100 milliseconds to 500 milliseconds. For example, the analog detail monitor can be capable of monitoring, collecting and storing a detailed pressure versus time profile over several minutes with a sampling rate of 100 milliseconds.

The system, the method, and the computer assisted method can have a plurality of configuration libraries. The plurality of configuration libraries can include a digital input monitor configuration library, an analog input monitor configuration library, a site task device configuration library, a data transfer device configuration library, an analog detail monitor configuration library or a site process monitor configuration library.

In an embodiment, the digital input monitor configuration library can include a site identifier (ID); a database connection information; a digital data acquisition hardware and bit configuration; an unused bit mask; a power-on, a lamp test, and an alarm bit identification; a digital data acquisition hardware read and poll intervals; and an identifier for the software driver used to communicate with the digital data acquisition hardware.

In an embodiment, the analog input monitor configuration library can include the site identifier (ID), the database connection information, the analog data acquisition hardware and I/O configuration, an unused I/O channel mask, the significant voltage or current change thresholds, the analog data acquisition hardware read and poll intervals, and an identifier for the software driver used to communicate with the analog data acquisition hardware.

In an embodiment, the analog detail monitor configuration library can include the site identifier (ID), the database connection information, the analog data acquisitions hardware and I/O configuration, an unused I/O channel mask, the sampling rate, the size of the sampling window, and an identifier for the software driver used to communicate with the analog data acquisition hardware.

In an embodiment, the site task device configuration library can include the site identifier (ID), the database connection information, and the wait interval for checking to see if there are any tasks to perform.

In an embodiment, the data transfer device configuration library can include the site identifier (ID), the database connection information, the wait interval between data transfers, and the maximum number of data elements transferred in any one transfer cycle can be included as one of the plurality of libraries.

In an embodiment, the site process monitor configuration library can include the site identifier (ID), the database connection information, an identifier for each process to be monitored including a type of process indicator, the maximum allowable restarts for any failing process, the time interval for checking on the monitored processes, and a system startup hold-off time interval.

The system, the method, and the computer assisted method can have site web server computer instructions in the site data storage to allow web access to the site data storage, site web server computer instructions in the site data storage to receive a request for status of the site processor, or combinations thereof.

The request for status can take the form of a web report. The web report can summarize the most recent messages and reports that were generated by the various monitors and devices, the last time each monitor and device completed a cycle, and the last time any sensor data was sent to the administrative server.

At a secondary location, the system, the method, and the computer assisted method can have an administrative server in communication with a site via a network, such as the Internet. The administrative server can have an administrative processor.

It is important to make a distinction between the data that can be generated at the site and the data that can be ultimately presented to the end user. The sensor data can be captured by the site processor and can be viewed as raw data. This raw data can be transferred to the administrative server and stored. The administrative server can generate various user reports and displays from this raw data.

The administrative server can transform the raw data into useful information, performing various analyses and correlations on the raw data or information, and presenting this information to the end user, so that the user can easily and quickly understood the information.

It is not anticipated that an end user have access to the site processor or that there is a local program or function on the site processor for the end user to use. An end user at the site, like other remote end users can log onto an administrative server to view information regarding the equipment at the drilling site.

The system, the method, and the computer assisted method can have an administrative data storage in the administrative server. The administrative data storage can have an administrative process monitor, an administrative site monitor, an administrative task device, or an administrative task transfer device.

The administrative process monitor can initiate and monitor the administrative site monitor, the administrative task device, and the administrative task transfer device. The administrative process monitor can periodically check on the status of each monitor and device. If one of the monitors or the devices is malfunctioning, the administrative process monitor can restart each malfunctioning monitor or device.

The administrative site monitor can periodically send a message to each site being monitored to determine if the site is functioning correctly and that the communication link to the site is working. If the administrative site monitor does not receive a response from the particular site, the administrative site monitor can generate a message in the administrative server database.

The administrative task device can be similar to the site task device. The administrative task device can perform various utility tasks on the administrative server. The administrative task device can check the database to see if there are any tasks it should perform. If a task is found, the administrative task device can perform the task and report the results to the database.

The administrative task transfer device can transfer tasks to be performed on one of the sites to the site's database. The administrative task transfer device can check the administrative database to see if there are any tasks to transfer to one of the sites. If a task is found, the administrative task transfer device can transfer the task to the appropriate site database. If the transfer is successful, the task can be marked in the database as having been transferred.

The administrative server can have a plurality of administrative configuration libraries, or combinations thereof. In an embodiment, the plurality of administrative configuration libraries can include an administrative process monitor configuration library, an administrative site monitor configuration library, an administrative task device configuration library, or an administrative task transfer device configuration library.

The administrative process monitor configuration library can include information, such as an identifier for each process to be monitored including a type of process indicator, database connection information, the maximum allowable number of restarts for any failing process, the time interval for checking the processes, a system startup hold-off time interval, or combinations thereof.

The administrative site monitor configuration library can include information, such as an identifier for each site being monitored, database connection information, the time wait interval between site monitoring requests.

The administrative task device configuration library can include database connection information, or information related to the time wait interval between checks to see if there are any tasks to perform, or combinations thereof.

The administrative task transfer device configuration library can include database connection information, or information on the time wait interval between checks to see if there are any tasks to transfer to various sites, or combinations thereof.

The administrative data storage can have computer instructions for forming an administrative database. The administrative database can store sensor data from the site. The administrative database can include a name of each piece of equipment at the site being monitored, a model number, an age, and specification information on the equipment, such as information on how to replace the equipment and the cost of the equipment.

Additional database information can include a timestamp to indicate when a data item is saved to the database. Data items can include an analog voltage data, a digital data, an error or information message, or an error or information report.

The administrative data storage can have computer instructions for forming an administrative web server. The administrative web server can receive and store the sensor data to the administrative data storage. The sensor data can be transmitted from the site to the administrative web server via the network.

The administrative data storage can have computer instructions for receiving, verifying, and storing site signals.

The administrative data storage can have computer instructions for combining a plurality of site signals with site configuration information to generate site data for the plurality of equipment at the site.

In an embodiment, the site configuration information can be site information, site control information, site control valve information, user security information, or site pressure information. Site information can include details about the site, such as the location of the drilling rig, the IP address, rig identification number, or combinations thereof.

Site control information can include details about the controls, such as the functions of the control or the mapping between the digital sensor data and the control. The site control valve information can include details about the valve, such as maximum cycles of the valve, the valve type, the valve location, the valve function, or combinations thereof.

The user security information can include security-related information for a user to access the administrative server. To access the administrative server, a user must input certain security-related information. Each user has a security profile that determines what the user can access on the administrative server.

Site pressure information can include details about the site pressures, such as pressure type, pressure range, or combinations thereof.

For example, sensor data received from a site can be combined with the site's digital and control configuration data to determine which controls may have changed states. The derived control state information can be stored in the administrative database. The derived control state information can be combined with the sites control valve configuration information to determine which valves were cycled as a result of the control state change. The control valve cycle information can be stored in the administrative database.

In an embodiment, the site data can include control state data, control cycle data, control valve data, pressure data, or combinations thereof.

The administrative data storage can have computer instructions for presenting at least one control state to a user, computer instructions for presenting at least one pressure data to a user, computer instructions for presenting at least one valve cycle to a user, or computer instructions for presenting at least one control cycle to a user.

In an embodiment, the computer instructions for presenting at least one control state to a user can include computer instructions to present a site description, computer instructions to present a page address, or computer instructions to present a last report date and time from the site. An example of a time stamp can be the date and time a piece of equipment made a transition to a new state on the site, when a signification voltage or current change was detected, or when a digital value change was detected.

In an embodiment, the computer instructions for presenting at least one control state to a user can include computer instructions to present a menu of reports, a presentation, a documentation, or a user administration item for selection by a user.

In an embodiment, the computer instructions for presenting at least one control state to a user can include computer instructions to present a calendar allowing a user to select a date for viewing. In an embodiment, the calendar is by days of the month. The user can pick a date on the calendar.

In an embodiment, the computer instructions for presenting at least one control state to a user can include computer instructions enabling a user to select a time scale for viewing. A variety of time scales can be selected, such as four weeks, one week, 24 hours, 12 hours, six hours, one hour, or some other time scale. Additional computer instructions can provide tic marks on a resulting chart enabling a visual subdivision of the time scale.

Additional computer instructions can be provided enabling the production of a time scale report for selected control. The time scale report can include a name of site equipment, a state of a control selected at the site during a selected time scale, visual indicator which indicate different states of the control during the selected time scale.

The indicators can be colors which are coded for each state of the control. The states of the control can include (i) unknown state; (ii) block or vent state, (iii) open state, or (iv)

closed state. The unknown state can be blue, the block or vent can be yellow, the open state can be green, or the closed state can be red for easy visual viewing to quickly stop damage or act promptly on the equipment. Other color to control state associations can be possible, but this depends on the site and the type of equipment being monitored.

In an embodiment, the computer instructions for presenting at least one control state to a user can include computer instructions enabling a user to select a control or a group of controls for viewing. A control or a group of controls for viewing can include blowout preventer controls, such as an upper annular preventer or a lower annular preventer. Other controls can include an upper ram, a middle ram, a lower ram, various choke and kill lines, a riser connector, a wellhead connector, or combinations thereof.

In an embodiment, the computer instructions for presenting at least one control state to a user can include computer instructions enabling a user to clear a list of at least one control. For example, the upper annular control and the lower annular control may have been checked. The user can then click the "clear" button and view the choke and kill line controls instead.

In an embodiment, the computer instructions for presenting at least one control state to a user can include computer instructions enabling a user to refresh at least one item presented to the user that is a time based item. An example of an item that is a time-based item can be the state of a blowout preventer ram or an annular control.

In an embodiment, the computer instructions for presenting at least one control state to a user can include computer instructions enabling a user to view an identifier for the site being monitored. An identifier can be an alpha code, a numeric code, a bar code, a photograph, a diagram, a schematic, a name, or combinations thereof.

In an embodiment, the computer instructions for presenting at least one control state to a user can include computer instructions for presenting a time stamp to a user indicating when information to a requested status response was provided to the administrative server from the site processor.

In an embodiment, the computer instructions for presenting at least one control state to a user can include computer instructions for allowing a user to shift the time scale. These computer instructions allow a user to shift a time scale 2 hours later, 2 hours earlier, 4 hours later, 4 hours earlier, 24 hours later, 24 hours earlier, or other combinations thereof of time shifts.

In an embodiment, the computer instructions for presenting at least one control state to a user can include computer instructions for providing a start date and time for a chart requested by the user.

In an embodiment, the computer instructions for presenting at least one control state to a user can include computer instructions for providing a chart legend to the user for the chart. A chart legend can include the color, such as red, green, yellow, blue, black, gray, or other color used to represent each control state for each control. For example, the color green can be used to indicate that a blowout preventer ram is open, and red can be used to indicate that the blowout preventer ram is closed.

In an embodiment, the computer instructions for presenting at least one control state to a user can include computer instructions providing a time code for a chart start date and time, a chart midpoint time, and a chart end date and time, or combinations thereof.

In an embodiment, the computer instructions for presenting at least one control state to a user can include computer instructions to provide a time scale report for a selected control using color.

In an embodiment, the computer instructions for presenting at least one pressure data to a user can include computer instructions to present a site description, such as a photo, or a name or another type of identifier.

In an embodiment, the computer instructions for presenting at least one pressure data to a user can include computer instructions to indicate a page address to a user to indicate which report, presentation, or web page is visible to a user. The administrative website can use a page address, or a page description, to give the user a hint of where the user is located within the website.

In an embodiment, the computer instructions for presenting at least one pressure data to a user can include computer instructions to present a last report date and time from the site, computer instructions to present a menu of reports, a presentation, a documentation, and a user administration item for selection by a user, or computer instructions to present a calendar allowing a user to select a date for viewing.

In an embodiment, the computer instructions for presenting at least one pressure data to a user can include computer instructions to enable a user to clear a list of at least one pressure type, computer instructions enabling a user to select a time scale for viewing, computer instructions to enable a user to select at least one pressure type for viewing, computer instructions for presenting a type of pressure, or computer instructions to enable a user to refresh at least one item presented to the user that is a time based item In an embodiment, the computer instructions for presenting at least one pressure data to a user can include computer instructions to enable a user to view an identifier for the site being monitored, computer instructions for presenting a time stamp to a user indicating when information to a requested response was provided to the administrative server from the site processor, computer instructions for presenting a pressure scale to a user, computer instructions for allowing a user to shift the time scale, or computer instructions for presenting a hyperlink to a detailed pressure change report, computer instructions for providing a start date and time for a chart requested by the user.

The computer instructions for presenting at least one pressure data to a user can include computer instructions to provide a state change for each control related to the pressure change. For example, opening the upper annular control will correlate with changes in both the pilot pressure and the accumulator pressure.

In an embodiment, the computer instructions for presenting at least one valve cycle to a user can include computer instructions to present a site description. The site description can be a name, an address, a code, a picture or combinations thereof.

In an embodiment, the computer instructions for presenting at least one valve cycle to a user can include computer instructions to indicate a page address to the user to indicate which report, presentation or web page is visible to the user. The page address can be an address a page number within the presentation of pressure data or within the presentation of cycles to the user.

In an embodiment, the computer instructions for presenting at least one valve cycle to a user can include computer instructions to present a last report date and time from the site.

In an embodiment, the computer instructions for presenting at least one valve cycle to a user can include computer instructions to present a menu of reports, a presentation, a documentation, or user administration items for selection by the user.

In an embodiment, the computer instructions for presenting at least one valve cycle to a user can include computer instructions to enable the user to select a control or a group of controls for viewing, computer instructions to enable the user to clear a list of at least one control, or computer instructions to enable the user to refresh at least one item presented to the user that is a time based item.

In an embodiment, the computer instructions for presenting at least one valve cycle to a user can include computer instructions to enable the user to view an identifier for the site being monitored. The identifier can be an alpha code, a numeric code, a bar code, a photograph, a diagram, a schematic, or combinations thereof.

In an embodiment, the computer instructions for presenting at least one valve cycle to a user can include computer instructions for presenting a time stamp to a user indicating when information to a requested response was provided to the administrative server from the site processor, or computer instructions to provide a name of a control to the control cycle report with an additional hyperlink to an additional report.

In an embodiment, the computer instructions for presenting at least one valve cycle to a user can include computer instructions for providing a location for each control or each valve. The location can identify a physical location of the control or the valve at a site.

In an embodiment, the computer instructions for presenting at least one valve cycle to a user can include computer instructions for providing a number of cycles that each control or each valve experienced.

In an embodiment, the computer instructions for presenting at least one valve cycle to a user can include computer instructions to provide a valve type, computer instructions to provide the function of a control or valve, computer instructions to provide a cycle count maximum, or computer instructions to provide a percent of current cycle count compared to a cycle count maximum.

A detail of a selected control can be provided, such as the number of times a blowout preventer ram was opened or closed, or the number of times the selected control's shuttle valve was cycled can be shown.

The name of a control can be provided on the control cycle report with a hyperlink to additional reports.

The system, the method, and the computer assisted method can have at least one user client device in communication with the administrative server. The user client device can have a user display, a user processor, or a user data storage in communication with the user processor.

In an embodiment, the administrative data storage can include computer instructions for allowing a user to reset a cycle count for a valve or a control, computer instructions for allowing a user to enter a count number from which to initiate a count, computer instructions to display the current cycle count of a control or a valve, computer instructions to save cycle information, or computer instructions enabling a user to return to a previous screen without saving.

In an embodiment, the administrative data storage can include computer instructions to provide a control or valve description, computer instructions for allowing a user to see a visual schematic to select a valve for resetting a cycle count, computer instructions for allowing a user to input a description indicating a reason for resetting a valve or cycle count, or computer instructions to present a calendar allowing a user to select a date.

In an embodiment, the computer instructions for presenting at least one pressure change to a user can include computer instructions for selecting a pressure change detail, or computer instructions to clear a list of pressure changes.

In an embodiment, the computer instructions for presenting at least one pressure change to a user can include computer instructions for enabling a user to refresh at least one item presented to the user that is a time based item.

In an embodiment, the computer instructions for presenting at least one pressure change to a user can include computer instructions to generate a time dependent pressure detail chart. The time dependent pressure detail chart can include a profile parameter of a time duration and a pressure change during the pressure transition. The time duration can be from 30 seconds to 5 minutes on a fine time scale, such as a sampling rate of once every 100 milliseconds.

In an embodiment, the computer instructions for presenting at least one pressure change to a user can include computer instructions for presenting all pressures during any pressure transition. An example of this can include pressure changes for the pilot pressure, the accumulator pressure, and the rig air pressure.

The computer instructions to generate a time dependent pressure detail chart can include computer instructions for generating a title with time and date of a selected pressure change, computer instructions for presenting a pressure scale, or computer instructions for presenting a change in time, a change in pressure, or combinations thereof to characterize the pressure transition.

The computer instructions to generate a time dependent pressure detail chart can include a time scale, or a pressure legend.

In an embodiment, the computer instructions for presenting at least one pressure change to a user can include computer instructions for presenting a pressure to a user. The pressure can be determined on a time versus pressure scale by name of pressure type.

In an embodiment, the computer instructions for presenting at least one pressure change to a user can include computer instructions for presenting all pressures during any pressure transition, computer instructions for presenting a type of pressure, computer instructions for presenting a pressure scale to a user, computer instructions for presenting a start and end time scale, or computer instructions for providing a start date and time for a chart requested by the user.

In an embodiment, the computer instructions for presenting at least one pressure change to a user can include computer instructions for providing a time scale different from the start and end time scale, or computer instructions for presenting a pressure legend.

In an embodiment, the administrative data storage can have computer instructions to present a calendar allowing a user to select a date for viewing, computer instructions enabling a user to select a time scale for viewing, computer instructions for allowing a user to shift the time scale, computer instructions for providing a start date and time for a chart requested by the user, computer instructions for generating a start date and time of a control state interval, or computer instructions for generating a end date and time of a control state.

In an embodiment, the administrative data storage can have computer instructions for generating an indicator by color, or computer instructions for generating a time duration of a control state interval.

The computer assisted method can have computer instructions stored on computer readable mediums to monitor a status from a secondary location of a plurality of equipment on a drilling site, while simultaneously enabling preventive maintenance for each of a plurality of equipment on the drilling site.

The computer assisted method can have site computer instructions stored on a site data storage. The site data storage can be in communication with a site data processor.

The site data storage can have computer instructions for receiving and storing sensor data from at least one sensor attached to an equipment at the site.

The site data storage can have computer instructions for receiving a sensor signal by using a site processor in communication with the site data storage, verifying that the sensor signal has been received by the site processor, and storing the sensor signal in a database.

The site data storage can have computer instructions for forming a database for the sensor data.

The site data storage can have computer instructions for tracking digital input using a digital input monitor, computer instructions for tracking analog input from the data acquisition hardware using an analog input monitor in the site data storage, or computer instructions for tracking an analog detail using an analog detail monitor to obtain detailed operational information.

The site data storage can have computer instructions for transferring the digital input, the analog input, the analog detail, or combinations thereof, using a data transfer device in the site data storage.

The site data storage can have computer instructions for using a site task device in the site data storage to monitor the database, to identify a specific task, and to perform the specific task once the specific task has been identified.

The site data storage can have computer instructions for monitoring the digital input monitor, the analog input monitor, the analog detail monitor, the data transfer device, and the site task device by using a site process monitor to ensure each monitor or device is operating correctly.

The site data storage can have computer instructions for installing a plurality of site configuration libraries into the site data storage, computer instructions for using site web server computer instructions to create a site based website, and computer instructions for receiving at least one request for status from the administrative server.

The site data storage can have computer instructions for responding to at least one request for status using the site based website.

The computer assisted method can have secondary location computer instructions stored on an administrative data storage. The administrative data storage can be in communication with an administrative processor.

The administrative data storage can have computer instruction for transmitting at least one request for status to the site processor. The site processor can respond to the request and send the response back to the administrative processor via the network.

The administrative data storage can have computer instruction for receiving a response to the at least one request from the site processor, or receiving sensor data, messages and reports from the site data storage.

The administrative data storage can have computer instruction for transmitting at least one task to the site database using an administrative task transfer device, computer instructions for forming an administrative database, computer instructions for installing a plurality of administrative configuration libraries, or computer instructions for forming an administrative web server. The administrative web server can receive, verify, and store the plurality of site signals transmitted by the site processor.

The administrative data storage can have computer instruction for combining the site configuration information with the plurality of site signals to generate site data for equipment at the site, computer instructions for presenting at least one control state to a user, computer instructions for presenting at least one pressure data to the user, computer instructions for presenting at least one control cycle to the user, or presenting at least one valve cycle to a user.

The computer assisted method can include using at least one user client device to communicate with the secondary location. The user client device can have a user display, a user processor and a user data storage in communication with the user processor.

Turning now to the Figures, FIG. 1 is a diagram of the computer assisted method.

FIG. 1 is a diagram of the computer assisted method. The computer assisted method can have a site 6, such as an offshore oil rig. The site can be a plant, or another facility that utilizes multiple controls, multiple pressures or multiple valves.

There is site equipment 11, such as a valve 7, at the site 6. The site equipment can have sensors 10 attached to the site equipment 11.

The sensor data 9 from the sensors 10 attached to site equipment 11 can be transferred from the sensor to the data acquisition hardware 8.

The data acquisition hardware 8 can be connected to a data acquisition power supply 12. The data acquisition power supply is depicted as a "daq power supply".

A plurality of data signals 13A from the data acquisition hardware 8 can be transferred by wireless connection or wired connection to a site processor 14. The site processor 14 can have a site power supply 15. The site processor 14 can be in communication with a site data storage 16.

The site processor 14 can transfer a plurality of data signals 13b from the site data storage 16 over a network 19A and to an administrative server 50. The administrative server 50 can have an administrative processor 52 and an administrative data storage 54 in communication with the administrative processor 52.

The administrative server 50 can communicate over the network 19B for communication with one or more user client devices 58a, 58b.

The user client devices 58a, 58b can have a user display 59a, 59b, in communication with a user processor 60a, 60b and a user data storage 62a, 62b.

Figure 2:
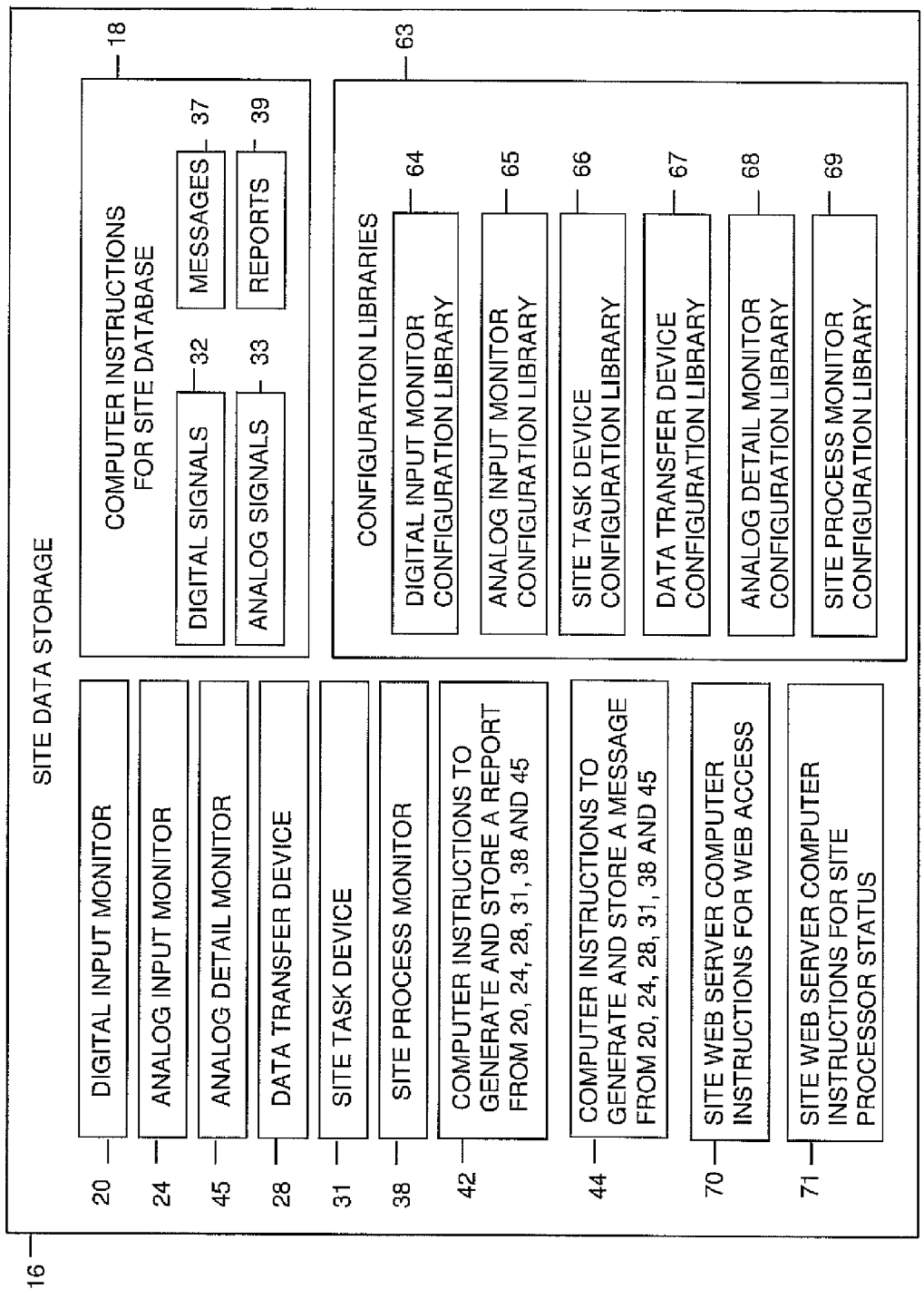
FIG. 2 is a diagram of the computer instructions within a site data storage.

FIG. 2 is a diagram of the computer instructions within the site data storage 16. The computer instructions in the site data storage can include the site process monitor 38, a digital input monitor 20, an analog input monitor 24, a data transfer device 28, an analog detail monitor 45, and a site task device 31.

The site data storage 16 can be depicted with the computer instructions for forming a site database 18, and computer instructions 42 for creating and storing at least one report from the digital input monitor 20, the analog input monitor 24, the data transfer device 28, the site task device 31, the site process monitor 38 and the analog detail monitor 45.

The site data storage 16 can also have computer instructions 44 for creating and storing at least one message on the digital input monitor 20, the analog input monitor 24, the data transfer device 28, the site task device 31, the site process monitor 38 and the analog detail monitor 45.

The site database can have at least one digital signal 32, at least one analog signal 33, at least one message 37, or at least one report 39.

The site data storage 16 can include a plurality of configuration libraries 63, which can include a digital input monitor configuration library 64, an analog input monitor configuration library 65, a site task device configuration library 66, a data transfer device configuration library 67, an analog detail monitor configuration library 68, and a site process monitor configuration library 69.

Examples of the information in these libraries can include the software driver associated with the data acquisition hardware, the database connection information, the hardware polling cycle, the masks to indicate unused control bits or analog I/O channels, control bits associated with a power-on, a lamp test, or an alarm.

The site data storage 16 can include site web server computer instructions 70 for creating a web server at the site and a site web server with computer instructions 71 to receive a request for status of the site processor.

Figure 3:
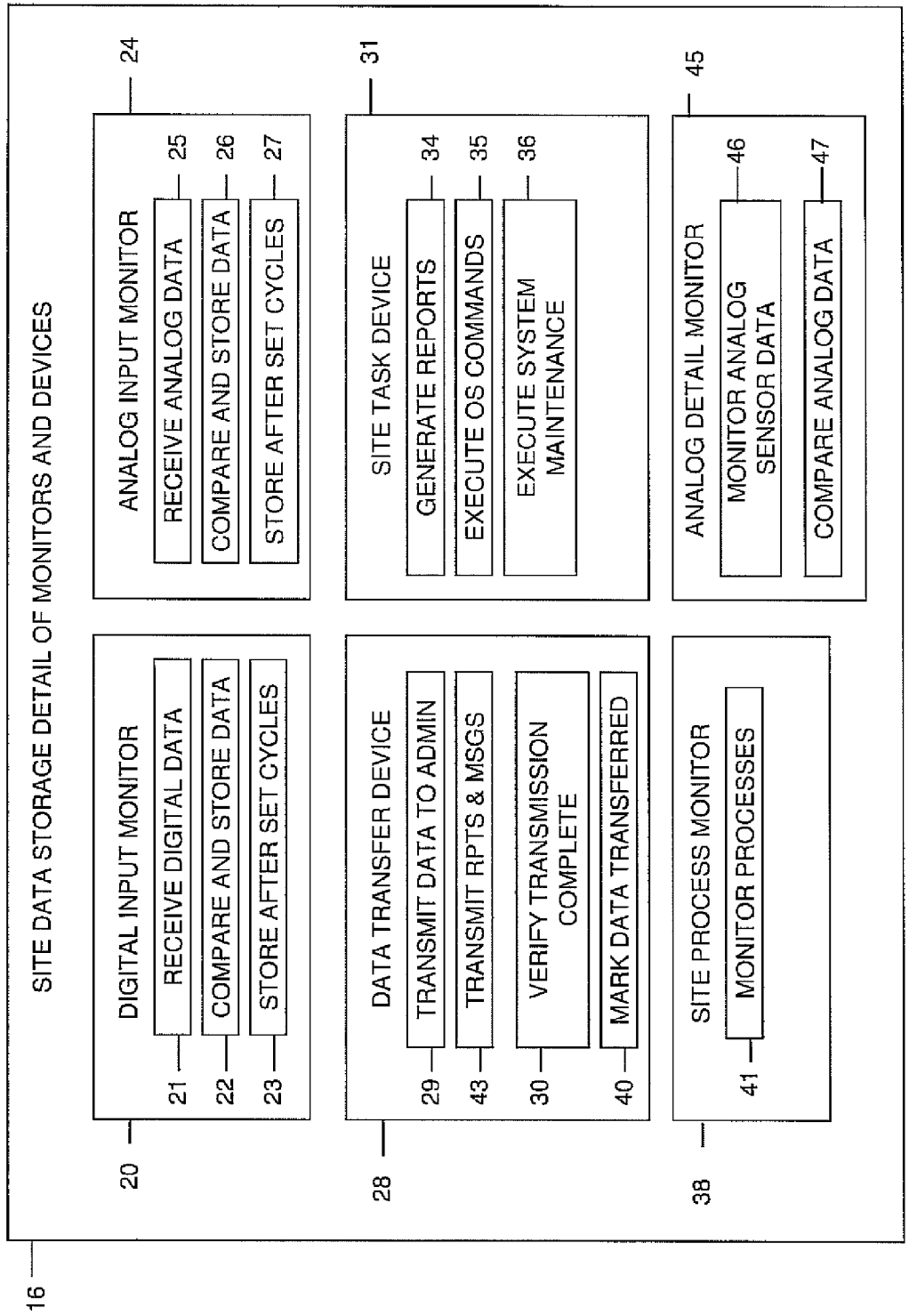
FIG. 3 is a depiction of the computer instructions within the monitors and devices of the site data storage.

FIG. 3 is a depiction of the computer instructions within the monitors and devices of the site data storage 16. FIG. 3 shows the site data storage 16 having a site process monitor 38. The site process monitor 38 can have computer instructions 41 to monitor status of the digital input monitor 20, the analog input monitor 24, the data transfer device 28, the site task device 31, and the analog detail monitor 45.

The digital input monitor 20 can have computer instructions 21 for receiving digital signals from the data acquisition equipment. The digital input monitor can have computer instructions 22 for comparing digital data to determine if a change in a digital signal occurs. The digital input monitor 20 can also store the data once a change occurs. A change in a digital signal refers to a change in an equipment state as indicated by a solenoid, a pressure switch, or other digital signal.

The digital input monitor 20 can have computer instructions 23 to store digital signals from the data acquisition equipment after a preset number of cycles, such as 25 cycles.

The analog input monitor 24 is depicted with computer instructions 25 for receiving analog sensor data from the data acquisition equipment, such as voltage or current associated with at least one analog signal.

The analog input monitor 24 can have computer instructions 26 to compare analog signals to determine if a change in an analog data occurs. The analog input monitor 24 can also store the data once a change occurs. These computer instructions can operate by comparing the voltage or current from the current reading with the voltage or current from the previous readings.

The analog input monitor 24 can have computer instructions 27 to store an analog signal after a preset number of cycles even if the change in reading is below a change threshold.

The data transfer device 28 can have computer instructions 29 for transmitting any sensor data stored by the digital input monitor, the analog detail monitor, or the analog input monitor. The data transfer device 28 can have computer instructions 43 for transmitting at least one report or at least one message for all of the programs running on the site processor.

The data transfer device 28 can have computer instructions 30 to verify the transfers of sensor data, the at least one report, or the at least one message is complete.

The data transfer device 28 can have computer instructions 40 for marking the sensor data, the at least one report, or the at least one message as transferred to the administrative server. The sensor data, the at least one report, or the at least one message can be marked with a transfer indicator to reflect if the data item has been successfully transferred or if it still needs to be transferred.

The site task device 31 can include computer instructions 34 to generate a report such as on disc utilization. The site task device 31 can include computer instructions 35 in the site data storage to execute an operating system utility command, or computer instructions 36 in the site data storage to perform another computer system maintenance activity.

The computer assisted method can have an analog detail monitor 45 in the site data storage. The analog detail monitor 45 can have computer instructions 46 in the site data storage for monitoring analog data from the data acquisition equipment. The analog detail monitor can have computer instructions 47 in the site data storage to compare analog sensor data to detect a change in analog sensor data.

The analog detail monitor can monitor sensor data on a rapid data sampling cycle and continuously save the sensor data to a data buffer. When the analog detail monitor detects a significant change in either voltage or current, additional data can be added to the buffer until a full window of data has been collected. When a complete window of data has been collected, it can be saved to the database.

Figure 4:
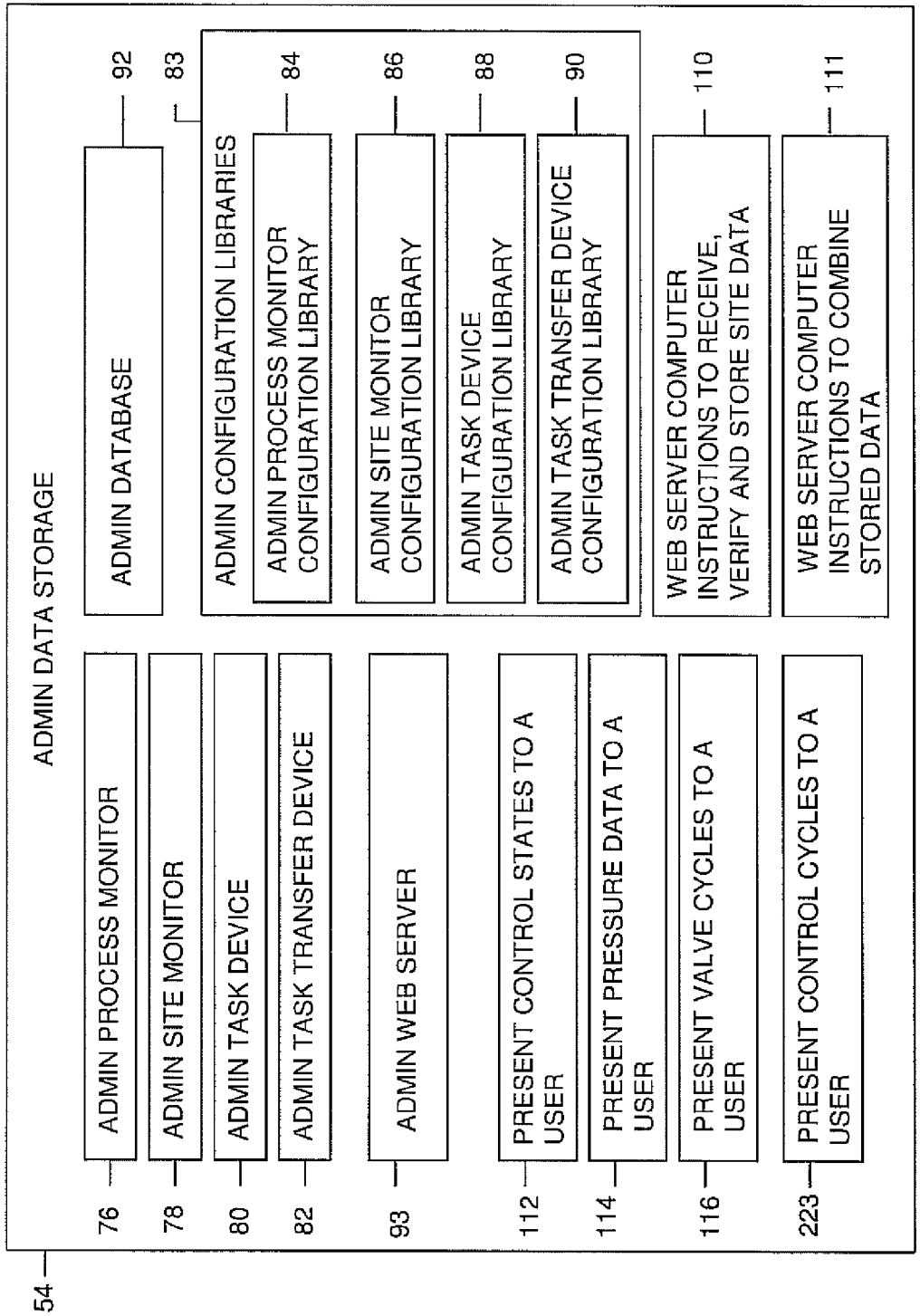
FIG. 4 is diagram of the computer instructions within the administrative data storage.

FIG. 4 is diagram of the computer instructions within the administrative data storage 54.

The administrative data storage 54 can have computer instructions to perform the steps of an administrative process monitor 76. Once the administrative process monitor is created, the administrative data storage 54 can have computer instructions to perform the steps of an administrative site monitor 78.

Once the administrative process monitor is created 76, the administrative data storage 54 can have computer instructions to perform the steps of an administrative task device 80.

Once the administrative process monitor 76 is created, the administrative data storage 54 can have computer instructions to perform the steps of an administrative task transfer device 82.

A plurality of administrative configuration libraries 83 can be stored in the administrative data storage 54, which can include an administrative process monitor configuration library 84, an administrative site monitor configuration library 86, an administrative task device configuration library 88, and an administrative task transfer device configuration library 90.

The administrative data storage 54 can include computer instructions 92 for forming an administrative database. The administrative database can store site information from a site via a site to administrative server network, which can be a satellite network, the Internet, a cellular network, another wireless network, or combinations of networks.

The administrative data storage 54 can include administrative web server computer instructions 93 to receive and store information transmitted over the network can be stored in the administrative data storage 54.

The administrative data storage 54 can include web server computer instructions 110 to receive, verify, and store site signals 97. The administrative data storage 54 can include web server computer instructions 111 for combining a plurality of site signals 97 with site configuration information 106 to generate site data 125 for the plurality of equipment at the site.

The administrative data storage 54 can include computer instructions 112 for presenting at least one control state to a user, computer instructions 114 for presenting at least one pressure data to a user, computer instructions 116 for presenting at least one valve cycle to a user, and computer instructions 223 for presenting at least one control cycle to a user.

Figure 5:
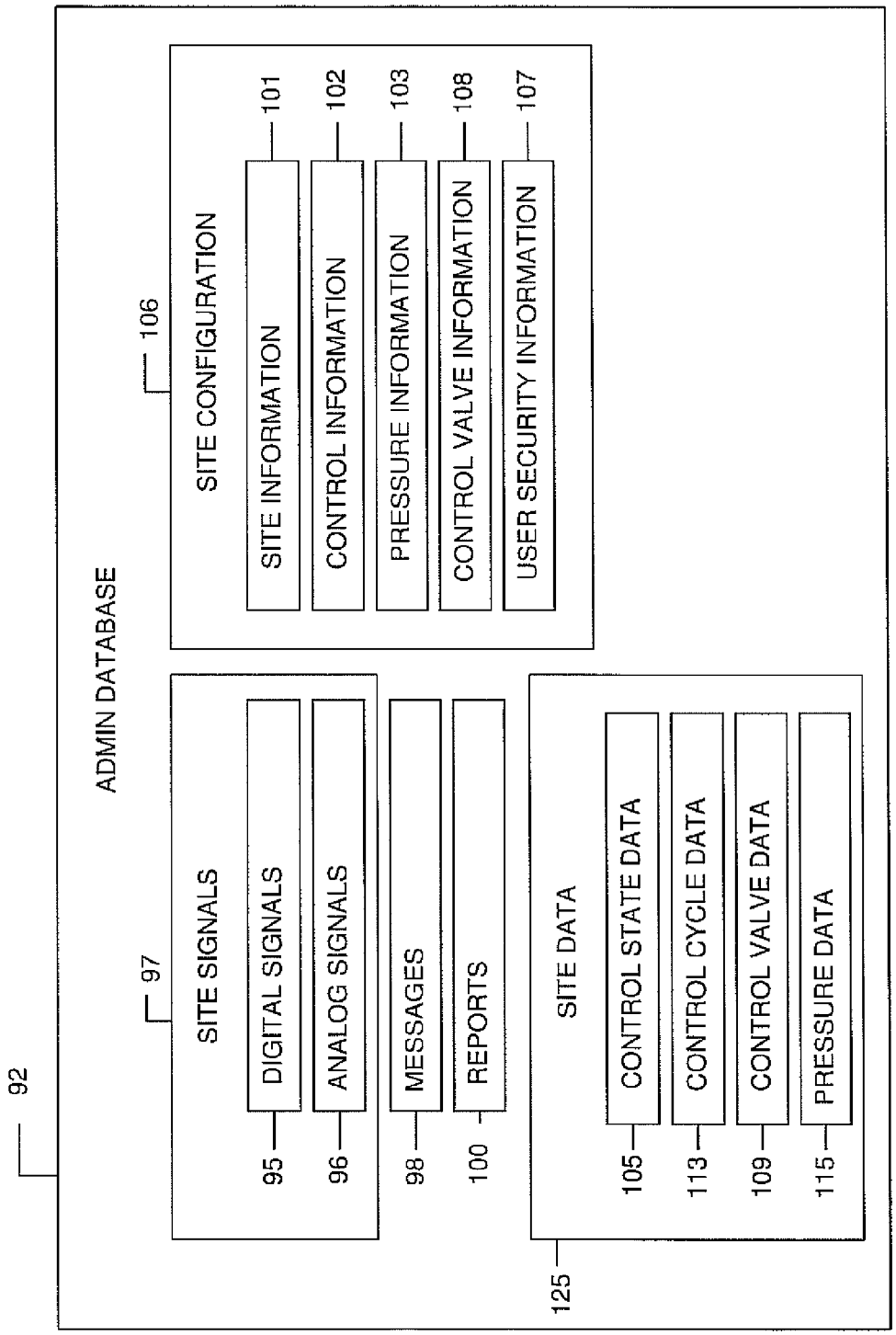
FIG. 5 is a diagram of components within the administrative database.

FIG. 5 is a diagram of components within the administrative database 92. The administrative database 92 can include computer instructions for combining a plurality of site signals 97 with site configuration information 106 to generate site data 125 for the plurality of equipment at the site.

The plurality of site signals 97 can include at least one digital signal 95, at least one analog signal 96, at least one message 98, or at least one report 100.

The site configuration information 106 can include site information 101, control information 102, pressure information 103, control valve information 108, and user security information 107.

The generation of site data 125 can include at least one control state data 105, at least one control cycle data 113, at least one control valve data 109, and at least one pressure data 115.

Figure 6:
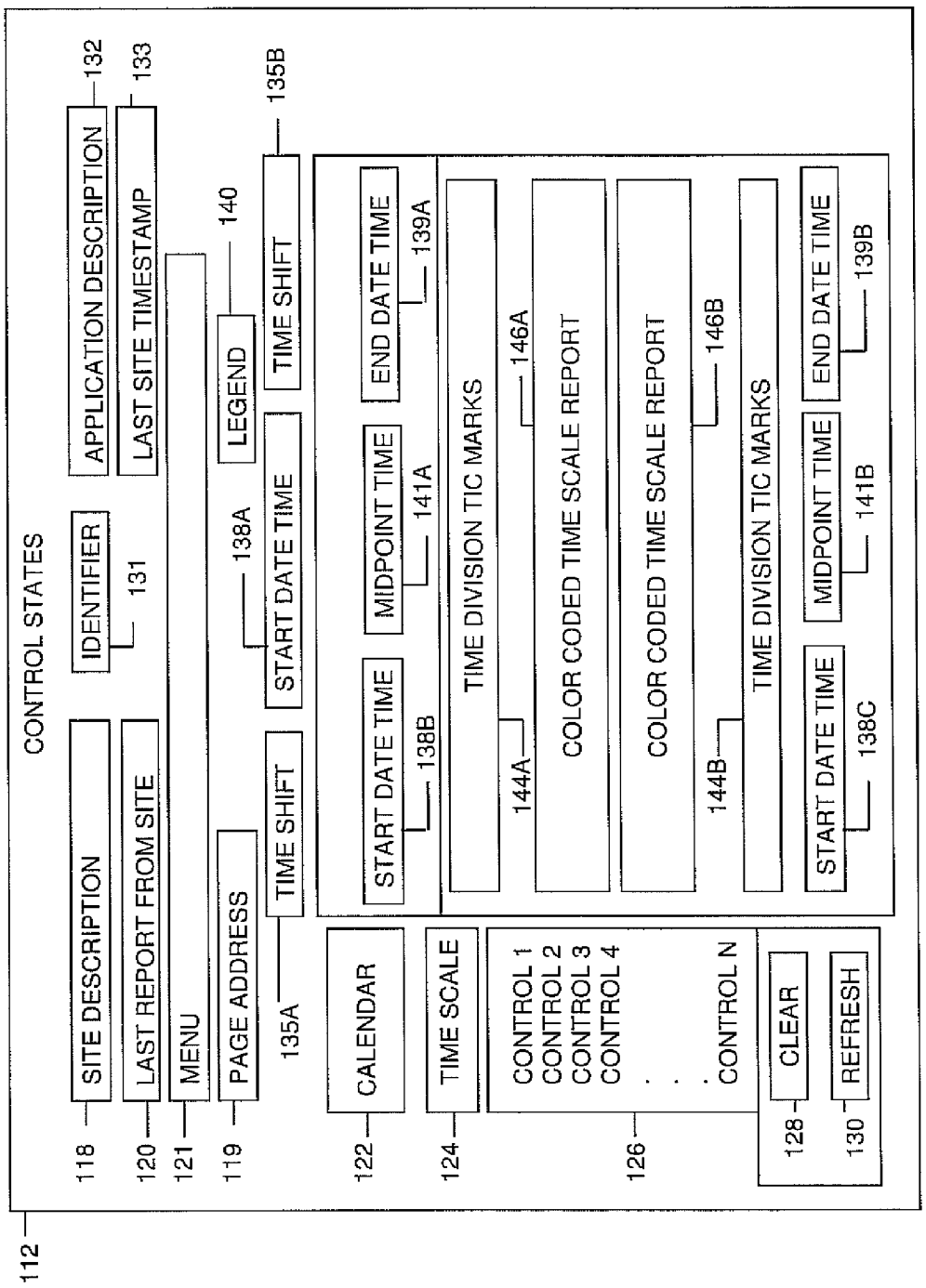
FIG. 6 is a page generated from computer instructions for presenting a plurality of control states to a user.

FIG. 6 is a page generated from computer instructions 112 for presenting at least one control state to a user.

The computer instructions 112 can include computer instructions 118 to present a site description, such as an address of the facility being monitored.

The computer instructions 112 can include computer instructions 119 to indicate a page address to a user as the page occurs within the website, computer instructions 120 to present a last report date and time from site, or computer instructions 121 to present a menu of reports, presentations, documentation, user administration for selection by a user.

The computer instructions 112 can include computer instructions 122 for allowing a user to select a date for viewing control states, and computer instructions 124 enabling a user to select a time scale for viewing control states.

The computer instructions 112 can include computer instructions 126 for selecting an individual or a group of controls for viewing, computer instructions 128 allowing a user to clear a list of selected individual controls or groups of controls, computer instructions 130 for enabling a user to refresh at least one item presented to the user that is a time based item, computer instructions 131 for presenting an identifier for the site being monitored, computer instructions 132 for presenting the application description, and computer instructions 133 to present a time stamp to a user indicating when information to a requested response was provided to the administrative server from the site processor.

The computer instructions 112 can include computer instructions 135A, 135B for allowing a user to shift the time scale, computer instructions 138A to provide a start date and time, and computer instructions 140 to provide a chart legend to the user for understanding any charts generated.

The computer instructions 112 can include computer instructions for providing a start date and time 138B, 138C, a chart midpoint time 141A, 141B, and a chart end date and time 139A, 139B, or combinations thereof.

The computer instructions 112 can include computer instructions 144A, 144B to provide tic marks to enable a visual subdivision of the time scale, and can include computer instructions 146A, 146B to provide a time scale report for each selected control including a name of site equipment from which monitoring data is obtained, a state of the control during a selected time scale, a visual indicator to indicate each different state for the control during the selected time scale. For example, green can represent open, red can represent closed, yellow can be unknown, or blue can be block or vent.

Figure 7:
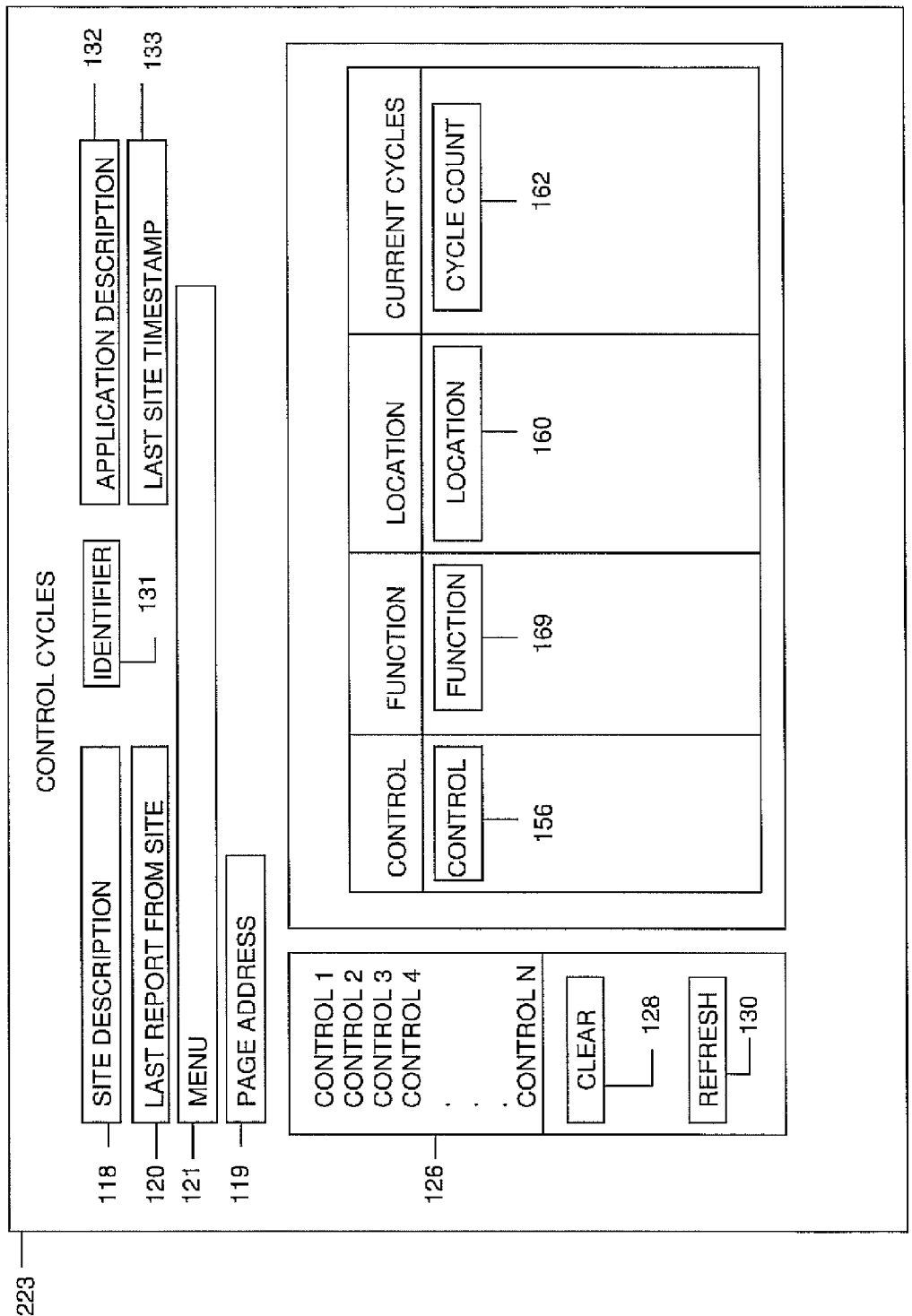
FIG. 7 is a page generated from computer instructions for presenting a plurality of control cycles to a user.

FIG. 7 is a page generated from computer instructions 223 for presenting a plurality of control cycles to a user. Computer instructions 223 can include computer instructions 118 to present a site description, such as an address of the facility being monitored.

The computer instructions 223 can include computer instructions 119 to indicate a page address to a user as the page occurs within the website, computer instructions 120 to present a last report date and time from the site, or computer instructions 121 to present a menu of reports, presentations, documentation, user administration for selection by a user The computer instructions 223 can include computer instructions 126 for selecting an individual or a group of controls for viewing, and computer instructions 128 for allowing a user to clear a list of selected individual controls or groups of controls.

The computer instructions 223 can include computer instructions 130 for enabling a user to refresh at least one item presented to the user that is a time based item, computer instructions 131 presenting an identifier for the site being monitored, computer instructions presenting an application description 132, and computer instructions 133 to present a time stamp to a user indicating when information to a requested response was provided to the administrative server from the site processor.

Computer instructions 223 can include computer instructions 156 to provide a name of a control to the control cycle report with a hyperlink to additional reports, computer instructions 169 to provide an identification of the function of a selected control, computer instructions 160 to provide a location for each selected control, and computer instructions 162 to provide a cycle count. The cycle count can be the number of cycles each control has undergone.

Figure 8:
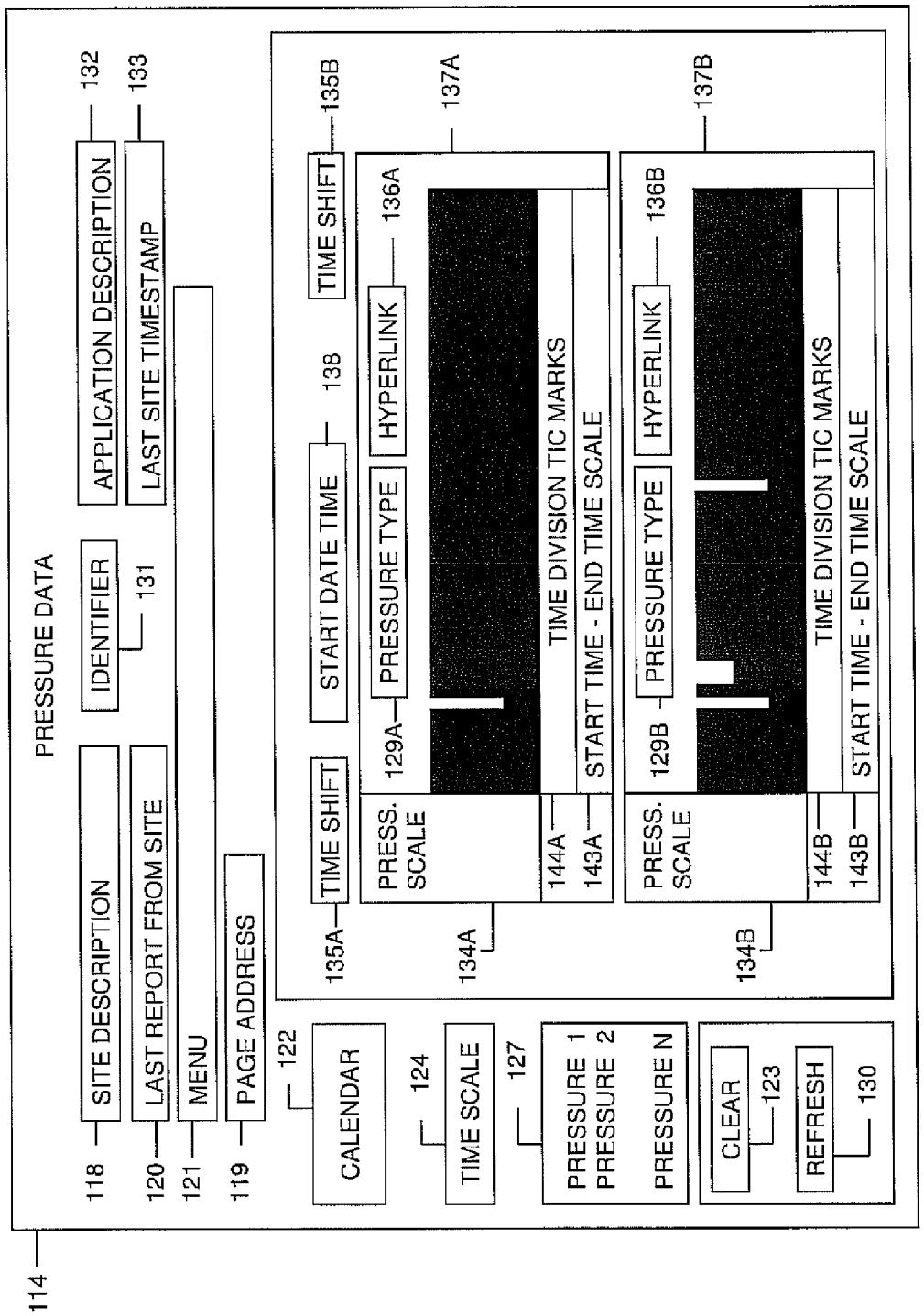
FIG. 8 is a page generated from computer instructions for presenting pressure data to a user.

FIG. 8 is a page generated from computer instructions 114 for presenting at least one pressure data to a user. The computer instructions 114 can have computer instructions 118 to present a site description, computer instructions 119 to indicate a page address to a user as the page occurs within the website, computer instructions 120 to present a last report date and time from site, and computer instructions 121 to present a menu of reports, presentations, documentations, user administration for selection by a user.

The computer instructions 114 can have computer instructions 122 to present a calendar allowing a user to select a date for viewing a pressure, computer instructions 124 enabling a user to select a time scale for viewing a pressure, computer instructions 127 for selecting an individual pressure or a group of pressures for viewing, computer instructions 123 allowing a user to clear a list of a selected individual pressures or a selected group of pressures, and computer instructions 130 for enabling a user to refresh at least one item presented to the user that is a time based item.

The computer instructions 114 can have computer instructions 131 for presenting an identifier for the site being monitored, computer instructions 132 for presenting the application description, and computer instructions 133 for presenting a time stamp to a user indicating when information to a requested response was provided to the administrative server from the site processor.

The computer instructions 114 can have computer instructions 134A, 134B for presenting a pressure scale, computer instructions 135A, 135B to provide a time shift scale control to a user, computer instructions 138 to provide a start date and time of the chart requested by a user, and computer instructions 137A, 137B for presenting a pressure graph.

The computer instructions 137A, 137B for presenting a pressure graph can include computer instructions 129A, 129B for presenting the pressure name, computer instructions 136A, 136B for presenting a hyper link, computer instructions 143A, 143B for presenting a start to end time scale, and computer instructions 144A, 144B to provide a tic mark to enable a visual subdivision of the time scale.

Figure 9:
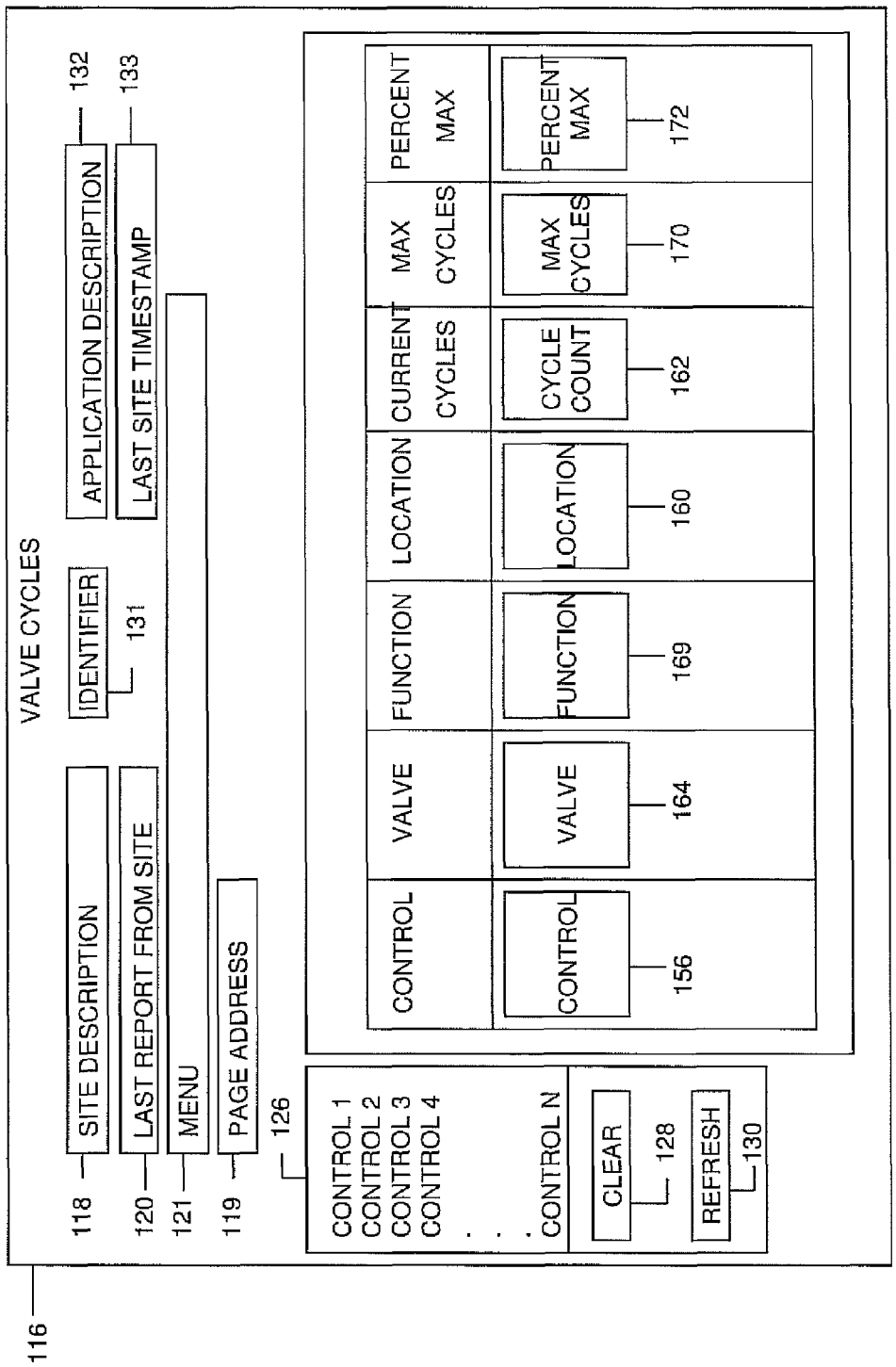
FIG. 9 is a page generated from computer instructions for presenting a plurality of valve cycles viewable by a user.

FIG. 9 is a page generated from computer instructions 116 for presenting at least one valve cycle viewable by a user.

Computer instructions 116 can include computer instructions 118 to present a site description, such as an address of the facility being monitored.

The computer instructions 116 can include computer instructions 119 to indicate a page address to a user as the page occurs within the website, computer instructions 120 to present a last report date and time from the site, or computer instructions 121 to present a menu of reports, presentations, documentation, user administration for selection by a user.

The computer instructions 116 can include computer instructions 126 for selecting an individual or a group of controls for viewing, and computer instructions 128 allowing a user to clear a list of selected individual controls or groups of controls.

The computer instructions 116 can include computer instructions 130 for enabling a user to refresh at least one item presented to the user that is a time based item, computer instructions 131 presenting an identifier for the site being monitored, computer instructions 132 presenting a description of the application, computer instructions 133 to present a last site time stamp to a user indicating when information to a requested response was provided to the administrative server from the site processor.

The computer instructions 116 can include computer instructions 162 to provide a cycle count, such as the number of times the valve opened, and a number of times the valve closed.

The computer instructions 116 can include computer instructions 156 to provide a control name, computer instructions 164 to providing a valve identification, such as a part number, and computer instructions 169 to provide the function of each valve or each control, as well as computer instructions 160 to provide a location of each valve or each control.

The computer instructions 116 can include computer instructions 170 to provide a cycle count maximum by valve as well as computer instructions 172 to provide a percent max, which is a percent of current cycle count compared to a maximum cycle count to a user for each valve selected.

Figure 10:
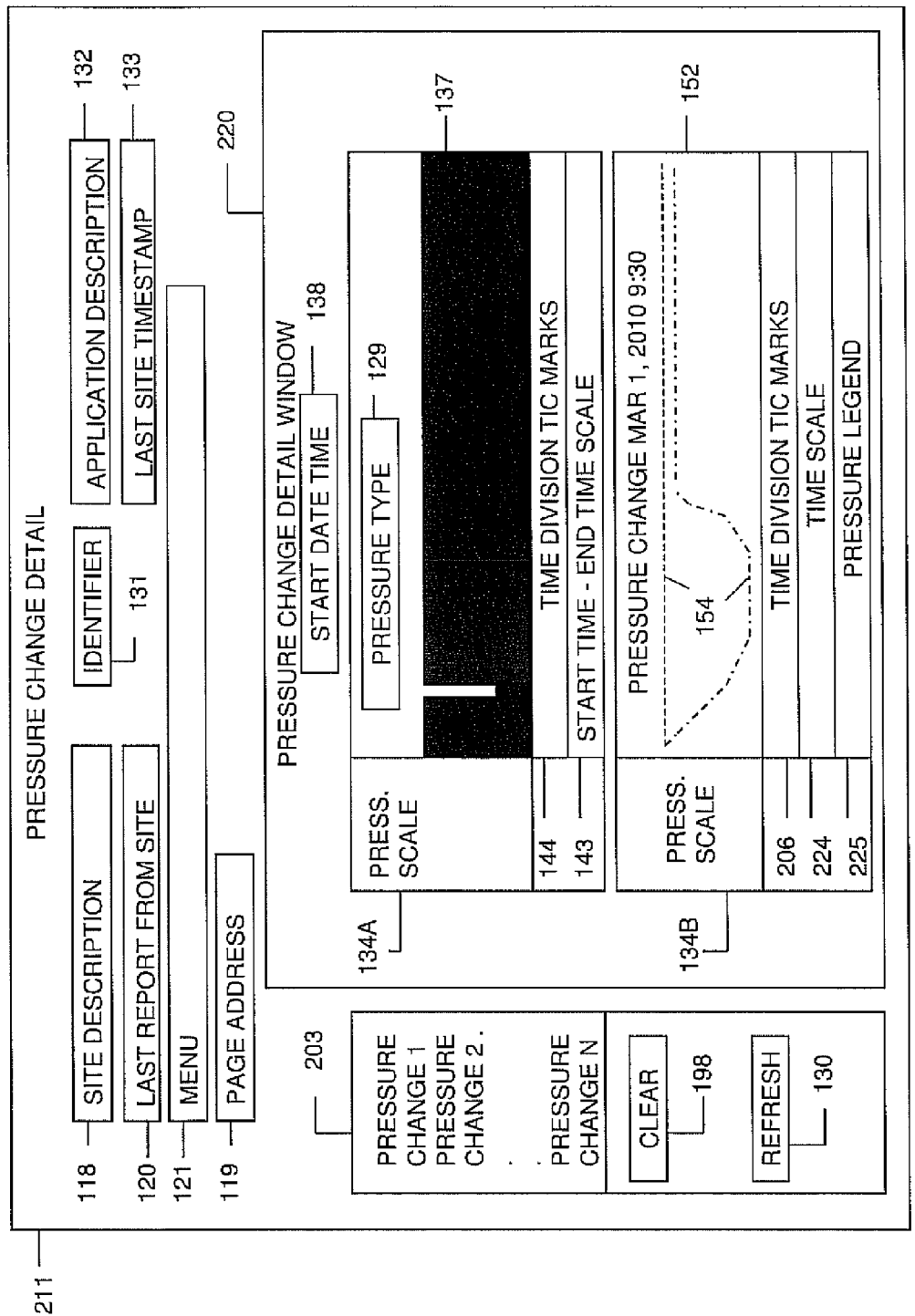
FIG. 10 is a pressure change detail page with a detailed 90 second view of a pressure change.

FIG. 10 is a pressure change detail page with a detailed 90 second view of a pressure change.

The pressure change detail page can have a site description 118, a site identifier 131, an application description 132, a last site timestamp 133A, 133B, a last report date from site 120, and a menu 121.

The pressure change detail page can indicate a page address 119 to a user as the page occurs within the website.

The pressure change detail page can have a pressure change detail window 220. The pressure change detail window 220 can indicate a pressure type 129. The pressure change detail window 220 can have a pressure history graph 137, and a pressure change graph 152. The pressure history graph 137 can have a pressure scale 134A, a time division tic mark 144, and a time scale 143. The pressure change graph 152 can have a pressure scale 134B, a time division tic mark 206, a time increment 224, and a pressure legend 225.

The pressure change detail page can have a select pressure change control 203, a clear all 198 of a list of selected individual pressure changes, and a refresh button 130 for enabling a user to refresh at least one item presented to the user that is a time based item.

Figure 11:
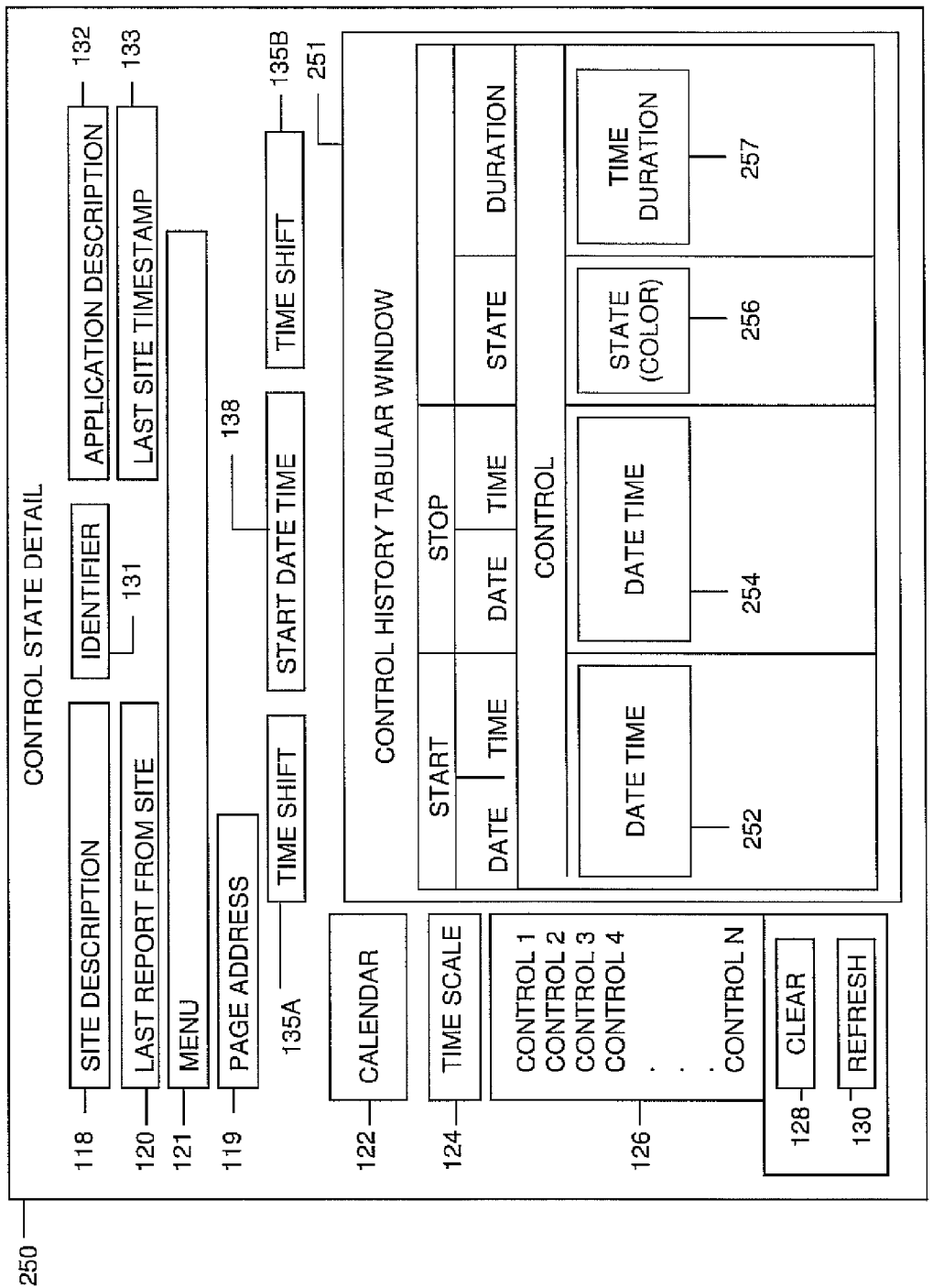
FIG. 11 is a control state detail page depicting the control states in more detail.

FIG. 11 is a control state detail page. The control state detail page can have a control history tabular window 251. The control history tabular window 251 can show each control state 256, the date and time the control entered the state 252, the date and time the control left the state 254, and the length of time the control remained in the state 257.

The control selection menu 126 can be used to add or remove a control from the report. The Clear All link 128 can be used to unselect all of the controls. The Refresh link 130 can allow a user to refresh at least one item presented to the user that is a time based item.

The control state detail page can include a description of the site 118, an application description 132, the time stamp 120 for the last report received from the site, and the last site time stamp 133A, 133B can be presented to a user to indicate when information to a requested response was provided to the administrative server from the site processor. The control state detail page can also include a menu 121 for selecting other reports and displays, and a page address 119 to help the user identify the current web page.

The control state detail page can include a calendar 122, a time scale selector 124, and a site identifier 131. The time scale selector can allow a user to select a time scale for the control state detail page.

The control state detail page can include a time shift 135A, 135B, and a start date and time 138.

Figure 12:
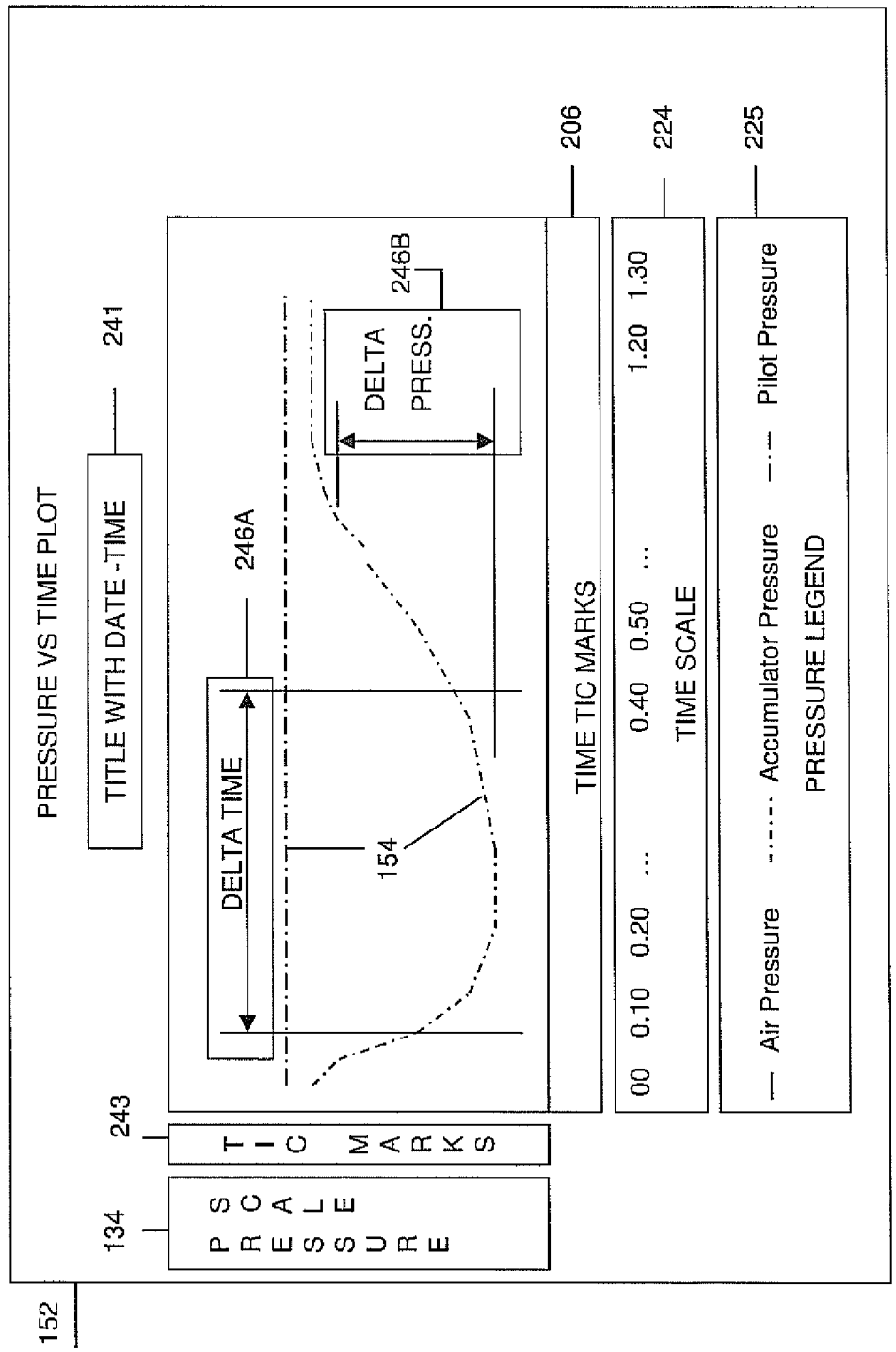
FIG. 12 is a pressure detail report for a 90 second interval.

FIG. 12 is a pressure detail report for a 90 second interval. The rig pressure detail report 152 can show the details of a pressure change over a small time window. The rig pressure detail page can have a graph of pressure versus time. The title 241 of the rig pressure detail report can indicate the date and time of the pressure change. The pressure scale 134 can be reported in pounds per square inch or another common pressure unit. The tic marks 243 can be used on the pressure scale to visually partition the scale.

The time scale of the graph 224 can be in seconds. The length the time scale 224 can range from 30 seconds to 180 seconds or longer if required. One or more pressures 154 can be shown in the pressure versus time display.

The pressures 154 can be distinguished by using colors or different line types. A legend 225 can correlate the color or line type with the pressure. The pressure versus time graph can characterize one or more of the pressure changes by using a profile, such as a delta time interval 246A, a delta pressure change value 246B, or combinations thereof. Time tic marks 206 can be illustrated within the pressure versus time graph.

Figure 13:
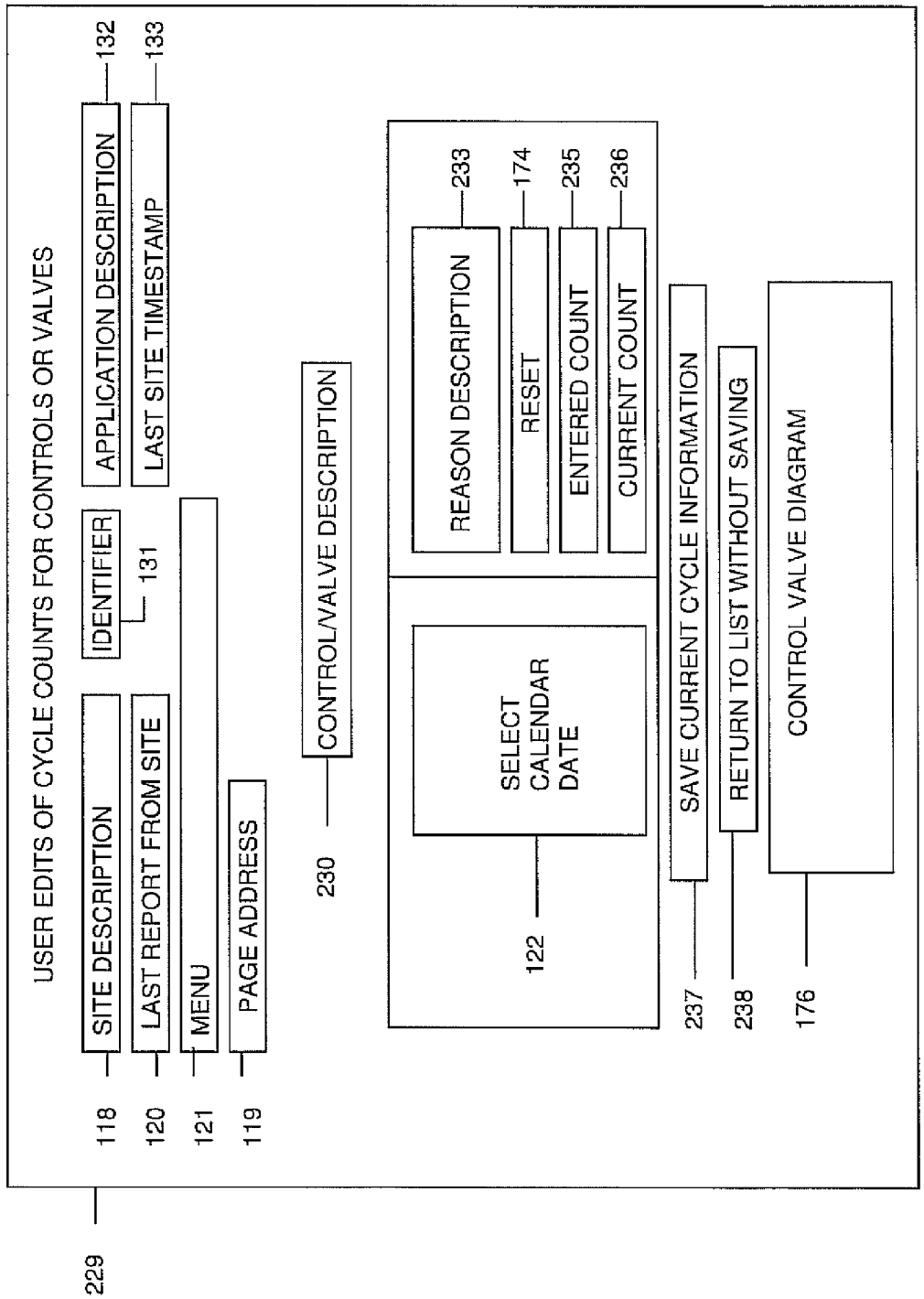
FIG. 13 is a page allowing a user to edit at least one cycle count for a valve cycle or control cycle as part of a maintenance record.

FIG. 13 is a page allowing a user to edit at least one cycle count for a valve cycle or control cycle as part of a maintenance record 229. The valve cycle or control cycle maintenance page 229 can show a diagram 176 that can document the valve configuration for the selected control. The user can select a valve from the diagram and change or reset the current number of cycles. This feature can be used when a valve is replaced or has been refurbished as part of the maintenance program.

The valve cycle or control cycle maintenance page 229 can include a description of the site 118, a description of the application 132, the site identifier 131, the time stamp 120 for the last report received from the site, the time stamp 133 can be presented to a user to indicate when information to a requested response was provided to the administrative server from the site processor. The valve cycle or control cycle maintenance page 229 can include a menu 121, for selecting other reports and displays and a page address 119 to help the user identify the current web page.

The valve cycle or control cycle maintenance page 229 can include a control type or valve type. The valve cycle or control cycle maintenance page 229 can include an add/cancel operation selection, a calendar date selection 122, a reason description 233, a change cycle count selection 174, an entered count selection 235, and a current count of valve cycles 236.

The valve cycle or control cycle maintenance page 229 can include a "save current cycle information" 237 functionality, and a return to list without saving 238 functionality.

Figure 14:
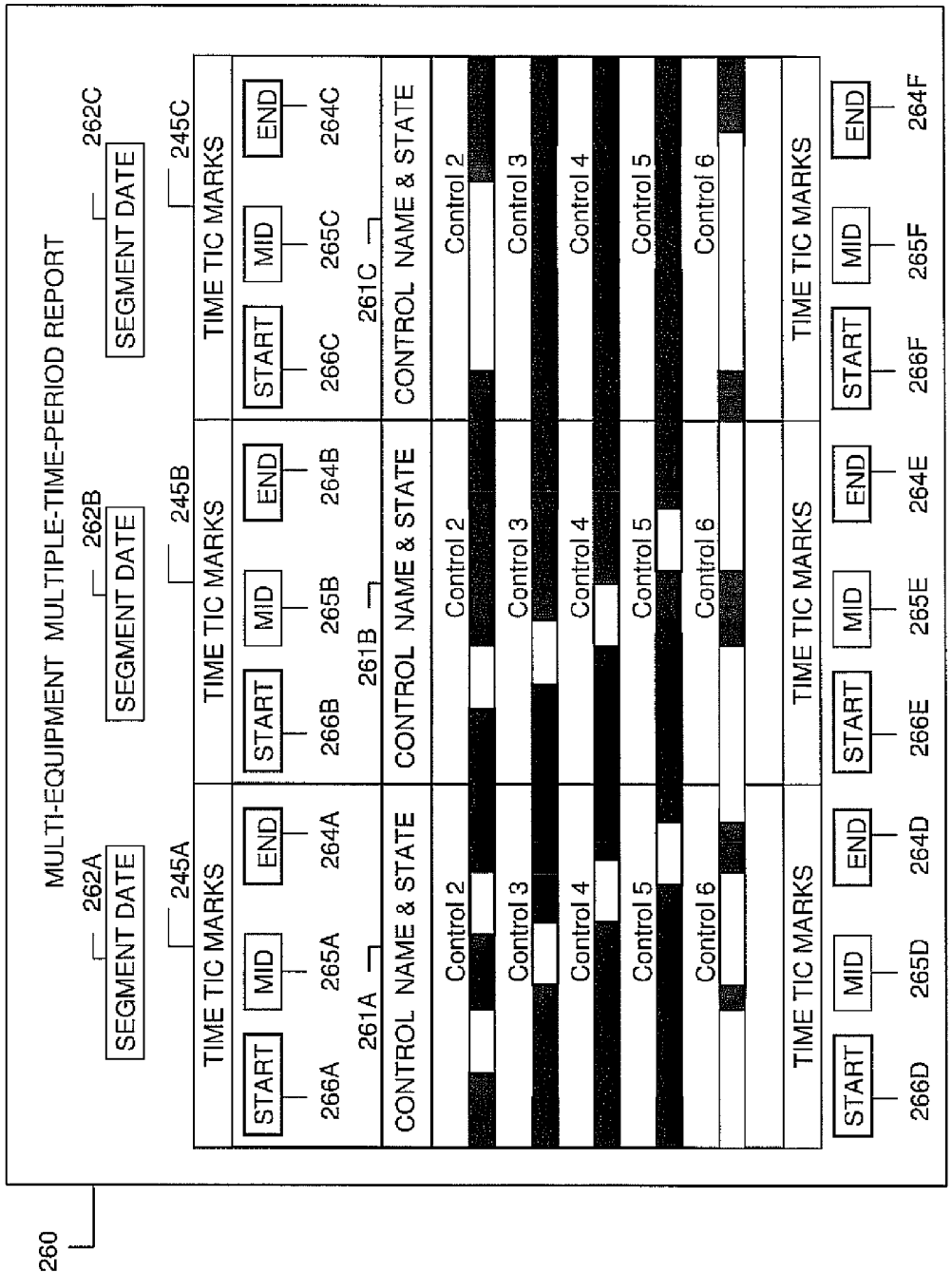
FIG. 14 is a depiction of a multi-equipment multi-time-period report as viewable by a user.

FIG. 14 is a depiction of a multi-equipment multi-time-period report 260 as viewable by a user. The multi-equipment multi-time-period report 260 can show multiple states of a plurality of equipment at the site, over a period of multiple days, as viewable by a user. The control state history can be viewed as a web page or as a PDF file.

The page 260 can give the user a convenient mechanism for viewing the control history, which can highlight a trend or event that occurred over several days. The control history can be generated for any number of days. For example, 5 days, 10 days, 14 days or another appropriate interval.

The multi-equipment multi-time-period report 260 can show a control name and state 261A, 261B, 261C. The multi-equipment multi-time-period report 260 can have at least one segment date 262A, 262B, 262C and a set of time tic marks 245A, 245B, 245C. Each segment can have a start segment time and date 266A, 266B, 266C, a mid segment date and time 265A, 265B, 265C, and an end segment time and date 264A, 264B, 264C.

Figure 15A:
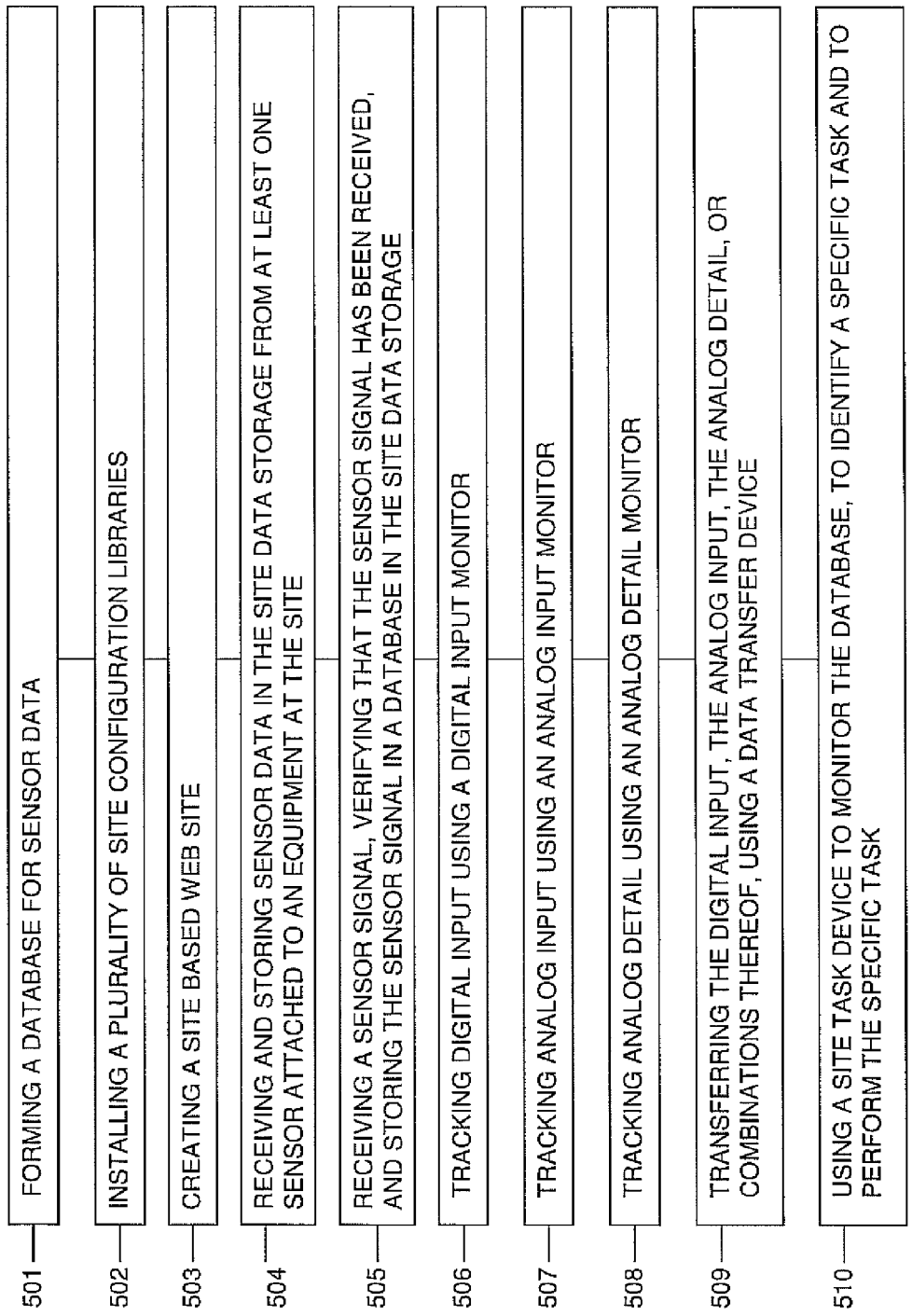
FIG. 15A is a diagram of the computer instructions involved in the computer assisted method.
Figure 15:
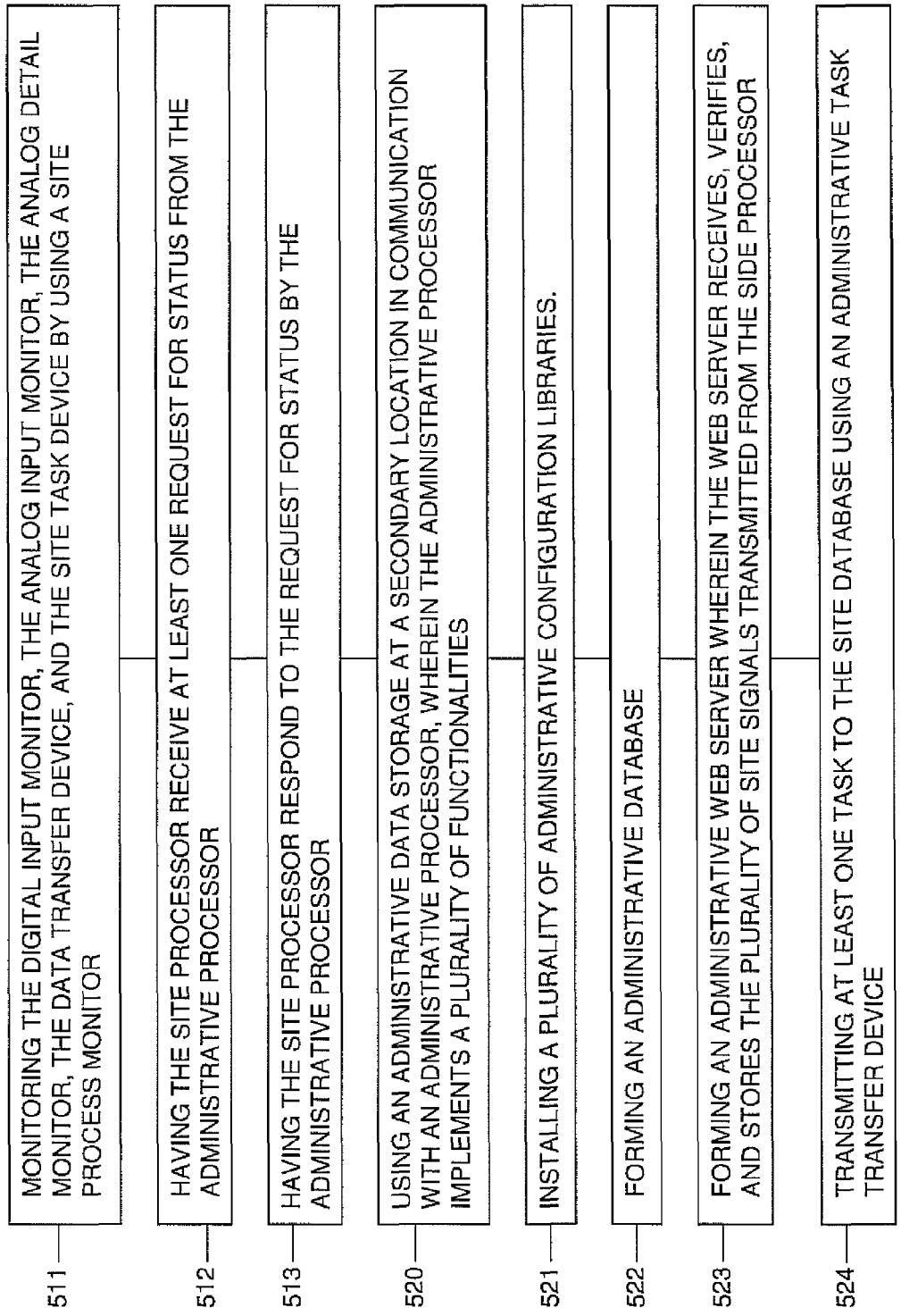
FIG. 15B is a continuation of FIG. 15B.
FIG. 15C is a continuation of FIG. 15B.
Figure 15:
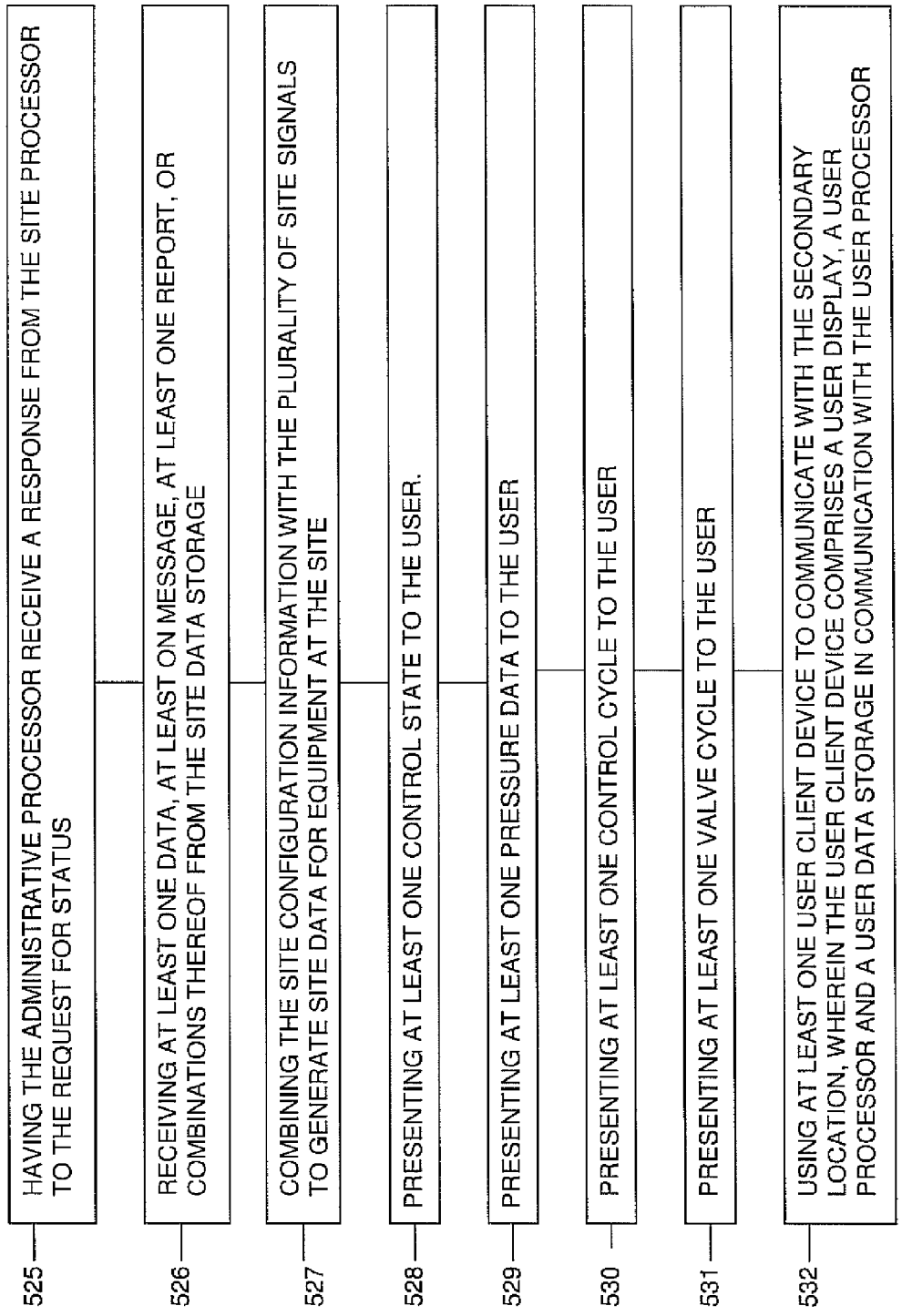

FIG. 15A is a diagram of the computer instructions involved in the computer assisted method.

The computer assisted method can include a site data storage, wherein the site data storage is in communication with a site data processor.

The site data storage can have computer instructions 501 for forming a database for the sensor data. The site data storage can have computer instructions 502 for installing a plurality of site configuration libraries, computer instructions 503 for creating a site based website.

The site data storage can have computer instructions 504 for receiving and storing sensor data in the site data storage from at least one sensor attached to an equipment at the site.

The site data storage can have computer instructions 505 for receiving a sensor signal, verifying that the sensor signal has been received, and storing the sensor signal in a database in the site data storage.

The site data storage can have computer instructions 506 for tracking digital input using a digital input monitor, computer instructions 507 for tracking analog input using an analog input monitor, computer instructions 508 for tracking an analog detail using an analog detail monitor, or computer instructions 509 for transferring the digital input, the analog input, the analog detail, or combinations thereof, using a data transfer device.

The site data storage can have computer instructions 510 for using a site task device to monitor the database, to identify a specific task and to perform the specific task.

FIG. 15B is a continuation of FIG. 15A.

The site data storage can have computer instructions 511 for monitoring the digital input monitor, the analog input monitor, the analog detail monitor, the data transfer device, and the site task device by using a site process monitor to ensure each monitor or device is operating correctly.

The site data storage can have computer instructions 512 of having the site processor receive at least one request for status from the administrative processor.

The site data storage can have computer instructions 513 of having the site processor respond to the request for status from the administrative processor.

The computer assisted method can have computer instructions 520 for using an administrative data storage in communication with an administrative processor.

The administrative data storage can have computer instructions 521 for installing a plurality of administrative configuration libraries.

The administrative data storage can have computer instructions 522 for forming an administrative database 92.

The administrative data storage can have computer instructions 523 for forming an administrative web server, wherein the web server receives, verifies, and stores the plurality of site signals transmitted from the site processor.

The administrative data storage can have computer instructions 524 for transmitting at least one task to the site database using an administrative task transfer device.

FIG. 15C is a continuation of FIG. 15B.

The administrative data storage can have computer instructions 525 for having the administrative processor receive a response from the site processor to the request for status.

The administrative data storage can have computer instructions 526 for receiving data, at least one message or at least one report from the site data storage.

The administrative data storage can have computer instructions 527 for combining the site configuration information with the plurality of site signals to generate site data for equipment at the site.

The administrative data storage can have computer instructions 528 for presenting at least one control state to a user.

The administrative data storage can have computer instructions 529 for presenting at least one pressure data to the user.

The administrative data storage can have computer instructions 530 for presenting at least one control cycle 223 to the user.

The administrative data storage can have computer instructions 531 for presenting at least one valve cycle 116 to the user.

The computer assisted method can have computer instructions 532 for using at least one user client device 58 to communicate with the secondary location, wherein the user client device comprises a user display 59, a user processor 60, and a user data storage 62 in communication with the user processor.

While these embodiments have been described with emphasis on the embodiments, it should be understood that within the scope of the appended claims, the embodiments might be practiced other than as specifically described herein.

What is claimed is:

1. A computer assisted method having computer instructions stored on non-transitory computer readable mediums to monitor a status from a secondary location of a plurality of equipment on a drilling site, while simultaneously enabling preventive maintenance, wherein the computer assisted method comprises:

a. site computer instructions stored on a site data storage, wherein the site data storage is in communication with a site data processor, wherein the site computer instructions comprise:
(i) computer instructions to form a database for sensor data;
(ii) computer instructions that installs a plurality of site configuration libraries;
(iii) computer instructions to create a site based website;
(iv) computer instructions to receive and store sensor data from at least one sensor attached to an equipment at the site;
(v) computer instructions to receive a sensor signal verifying that the sensor signal has been received, and store the sensor signal in a database;
(vi) computer instructions that track digital input using a digital input monitor;

(vii) computer instructions that track analog input using an analog input monitor;
(viii) computer instructions to monitor an analog detail using an analog detail monitor;
(ix) computer instructions to transfer the digital input, the analog input, the analog detail, or combinations thereof, using a data transfer device;
(x) computer instructions to use a site task device to monitor the database, to identify a specific task, and then to perform the specific task;
(xi) computer instructions to monitor the digital input monitor, the analog input monitor, the analog detail monitor, the data transfer device, and the site task device by using a site process monitor;
(xii) computer instructions to receive at least one request for status from an administrative server; and
(xiii) computer instructions to have a site processor respond to the at least one request for status from an administrative processor using the site based website;

b. administrative computer instructions stored on an administrative data storage at the secondary location, wherein the administrative data storage is in communication with the administrative processor, wherein the administrative computer instructions comprise:
(i) computer instructions that install a plurality of administrative configuration libraries;
(ii) computer instructions that form an administrative database;
(iii) computer instructions that form an administrative web server, wherein the web administrative server receives, verifies, and stores a plurality of site signals transmitted from the site processor;
(iv) computer instructions that transmits at least one task to a site database using an administrative task transfer device;
(v) computer instructions that transmits at least one request for status to the site processor;
(vi) computer instructions to receive a response to the at least one request from the site processor;
(vii) computer instructions to receive at least one data, at least one message, at least one report, and combinations thereof from the site data storage;
(viii) computer instructions that combine the site configuration information with the plurality of site signals to generate site data for equipment at the site;
(ix) computer instructions that presents at least one control state to a user;
(x) computer instructions that presents at least one pressure data change to the user;
(xi) computer instructions that presents at least one control cycle to the user; and
(xii) computer instructions that presents at least one valve cycle to the user comprising:
1. computer instructions that presents a site description, wherein the site description comprises a member of a group: a name, an address, a code, a picture or combinations thereof of the site;
2. computer instructions to indicate a page address;
3. computer instructions that presents a last report date and time from the site;
4. computer instructions that presents a menu of reports, presentations, documentation, and user administration items for selection by the user;
5. computer instructions that enables the user to select a control or a group of controls for viewing;
6. computer instructions that enables the user to clear a list of at least one control;
7. computer instructions that enables the user to refresh at least one item presented to the user that is a time based item;
8. computer instructions that enables the user to view an identifier for the site being monitored, wherein the identifier is an alpha code, a numeric code, a bar code, a photograph, a diagram, a schematic, or combinations thereof;
9. computer instructions that presents a time stamp to the user indicating when information to a requested response was provided to the administrative server from the site processor;
10. computer instructions that presents a name of a control to the control cycle report with an additional hyperlink to an additional report;
11. computer instructions that presents a valve type;
12. computer instructions for providing a function of each control or each valve;
13. computer instructions that presents a location for each selected control or each valve;
14. computer instructions that presents a number of cycles that each control or each valve experienced;
15. computer instructions that presents a cycle count maximum by selected valve; and
16. computer instructions that presents a percentage of a current cycle count as compared to the maximum cycle count for each valve selected, wherein the percentage is provided to the user;

c. computer instructions that enables at least one user client device to be in communication with the administrative server.

2. The computer assisted method of claim 1, wherein the secondary location computer instructions further comprises:
a. computer instructions that allows the user to reset a cycle count for each valve or each control;
b. computer instructions that allows the user to enter a cycle count number from which to initiate a count;
c. computer instructions that displays the current cycle count of each control or each valve;
d. computer instructions that saves cycle information;
e. computer instructions that enables the user to return to a previous screen without saving;
f. computer instructions that presents each control description or each valve description;
g. computer instructions that allows the user to see a visual schematic to select a valve for resetting each control cycle count or each valve cycle count;
h. computer instructions that allows the user to input a description to indicate a reason for resetting a valve or cycle count; and
i. computer instructions that allows the user to select a date for the cycle reset.

3. The computer assisted method of claim 1, wherein the computer instructions that presents at least one pressure change to the user further comprise:
a. computer instructions to select at least one pressure change detail;
b. computer instructions that clears a list of pressure change details;
c. computer instructions that generates a time dependent pressure detail chart, wherein a time duration is from 30 seconds to 5 minutes on a fine time scale;
d. computer instructions that presents a pressure to the user, wherein the pressure is determined on a time versus pressure scale by name of pressure type;
e. computer instructions that presents at least one pressure during any pressure transition;

f. computer instructions that presents a type of pressure;
g. computer instructions that presents a pressure scale to the user;
h. computer instructions that presents a start and end time scale;
i. computer instructions that presents a start date for a chart requested by the user;
j. computer instructions that presents a time scale for the pressure change, wherein the time scale for pressure change is different from the start and end time scale; and
k. computer instructions that presents a pressure legend.

4. The computer assisted method of claim 1, wherein the secondary location computer instructions further comprise:
   a. computer instructions that presents a calendar allowing the user to select a date for viewing;
   b. computer instructions that enables the user to select a time scale for viewing;
   c. computer instructions that allows the user to shift the time scale;
   d. computer instructions that presents a start date for a chart requested by the user;
   e. computer instructions that generates a start date and time of a control state interval;
   f. computer instructions that generates an end date and time of a control state interval;
   g. computer instructions that generates an indicator by color; and
   h. computer instructions that generates a time duration of a control state interval.

5. The computer assisted method of claim 3, wherein the computer instructions that generates a time dependent pressure detail chart further comprise:
   a. computer instructions that generates a title with time and date of a selected pressure change; and
   b. computer instructions that presents a change in time, a change in pressure, or combinations thereof to characterize the pressure transition.

\* \* \* \* \*